(12) United States Patent
Thorne

(10) Patent No.: US 6,972,002 B2
(45) Date of Patent: Dec. 6, 2005

(54) PASSIVELY ACTIVATED SAFETY SHIELD FOR A CATHETER INSERTION NEEDLE

(75) Inventor: David L. Thorne, Kaysville, UT (US)

(73) Assignee: Specialized Health Products, Inc., Bountiful, UT (US)

( * ) Notice: Subject to any disclaimer, the term of this patent is extended or adjusted under 35 U.S.C. 154(b) by 196 days.

(21) Appl. No.: 10/453,357

(22) Filed: Jun. 3, 2003

(65) Prior Publication Data

US 2003/0199827 A1 Oct. 23, 2003

Related U.S. Application Data

(62) Division of application No. 09/561,731, filed on Apr. 28, 2000, now abandoned.

(51) Int. Cl.[7] ............................................. A61M 5/178
(52) U.S. Cl. ................. 604/164.08; 604/198
(58) Field of Search ............................... 604/162, 263, 604/264, 164.07, 125, 193, 195, 197, 198, 604/170, 181, 187, 264.02, 110, 192, 164.01, 604/165.02

(56) References Cited

U.S. PATENT DOCUMENTS

| | | | |
|---|---|---|---|
| 3,848,593 A | 11/1974 | Baldwin | 128/218 |
| 4,762,516 A | 8/1988 | Luther | 604/164 |
| 4,828,548 A | 5/1989 | Walter | 604/164 |
| 4,950,252 A | 8/1990 | Luther | 604/198 |
| 4,964,854 A | 10/1990 | Luther | 604/166 |
| 5,000,740 A * | 3/1991 | Ducharme et al. | 604/162 |
| 5,176,655 A | 1/1993 | McCormick | 604/198 |
| 5,273,540 A | 12/1993 | Luther | 604/110 |
| 5,348,544 A | 9/1994 | Sweeney | 604/192 |
| 5,403,283 A | 4/1995 | Luther | 604/164 |
| 5,447,501 A | 9/1995 | Karlsson | 604/198 |
| 5,487,734 A | 1/1996 | Thorne | 604/195 |
| 5,501,675 A | 3/1996 | Erskine | 604/263 |
| 5,520,654 A | 5/1996 | Wahlberg | 604/164 |
| 5,562,629 A | 10/1996 | Haughton | 604/158 |
| 5,573,510 A | 11/1996 | Isaacson | 604/158 |
| 5,690,619 A | 11/1997 | Erskine | 604/263 |
| 5,795,339 A | 8/1998 | Erskine | 604/264 |
| 5,830,190 A | 11/1998 | Howell | 604/168 |
| 5,910,132 A | 6/1999 | Schultz | 604/162 |
| 5,911,705 A * | 6/1999 | Howell | 604/110 |
| 5,913,846 A | 6/1999 | Szabo | 604/263 |

FOREIGN PATENT DOCUMENTS

WO          WO 99/08742         2/1999 .......... A61M 25/06

* cited by examiner

*Primary Examiner*—Nicholas D. Lucchesi
*Assistant Examiner*—Matthew F. DeSanto
(74) *Attorney, Agent, or Firm*—Paul S. Evans; Mark S. Leonardo; Peter B. Sorell

(57) ABSTRACT

A passively activated shielding device for a catheter insertion needle. Disclosure of shielding devices according to the instant invention is provided in four embodiments. Unreleasible locking apparatus is the major differentiator in three of the devices. An accordionated or folded needle shield which markedly reduces preshielded length of one of the embodiments is the major differentiator in a fourth embodiment. Each embodiment employs a mechanical sensor which detects presence of the catheter insertion needle and its tip insertion needle within protective cover of a needle shield and passively responds to provide separation of the needle shield from an associated catheter assembly.

14 Claims, 35 Drawing Sheets

PASSIVELY ACTIVATED SAFETY SHIELD FOR A CATHETER INSERTION NEEDLE

RELATED CASE INFORMATION

This application is a Divisional of application Ser. No. 09/561,731 filed Apr. 28, 2000 now abandoned.

FIELD OF INVENTION

This invention relates generally to safety methods and apparatus for catheter introducer needles and specifically to safety methods and apparatus for catheter introducer needles which passively activate, requiring no additional steps other than those steps normally used in catheter introduction, to thereby prevent accidental contact with a sharpened tip of an introducer needle.

DESCRIPTION OF RELATED ART

Catheters for hypodermic procedures generally require an introducer needle having a sharpened tip for percutaneous entry. The catheters are commonly used to administer fluids and for access to body fluids most commonly via a patient's vascular system. Such catheters are often used in emergency situations where patient response is unpredictable and inadvertent needle sticks are likely to occur. Even under the best of circumstances, the nature of catheter insertion procedures and steps necessary to check and contain blood flow as a catheter insertion needle is removed from the catheter at the end of an insertion procedure creates an environment of significant risk for a health care worker.

For this reason, safety catheter introducer devices are increasing in popularity. Such safety devices range from mechanical devices where a sheath is manually extended over a needle to devices which automatically retract needles into a protective covering at the press of a button. Other safety devices blunt the sharpened tip of an insertion needle by extending a blunt member beyond the sharpened tip of an insertion needle.

More recently, passively activated safety catheter insertion devices have been introduced into commerce. One such device relies upon a needle tip guard which is housed in an attachable fitting such as a luer fitting while a catheter insertion needle is being employed in catheter introduction and which is automatically released from the fitting as the needle is removed from the catheter and is protectively affixed about the sharpened end of the needle as the needle is separated from the fitting. Another such device extends a blunting member beyond the sharpened end of a catheter insertion needle as a catheter is separated from a hub associated with a catheter insertion needle.

There are a number of factors which should be considered when evaluating a degree of worth and acceptability of various types of safety catheter insertion devices. These factors include ease of use, degree of safety and manufacturing cost. While these are not listed in order of importance or acceptance, ease of use is very important. If procedural changes are required to use a new device, in service training requirements are compounded. If the device is cumbersome to use, extra time may be required or inadvertent errors may be more common.

While it is relatively difficult to quantify a degree of safety of a device without sophisticated statistical studies being made, a number of primary observations may help assessment of effectiveness and acceptability of a safety device. Such observations should include analysis of any requirement for extra steps needed to activate a safety mechanism which could result in greater jeopardy of use. It is for this reason that passively activated devices are preferred. An evaluation of the structure of any safety shield or other safety enhancing part to assure that inadvertent bumping or other improper handling will not overcome any safety feature. Special note should be made of secondary items which may affect safety of a device such as any likelihood of being injured by an already activated safety device, such as being scratched by a needle blunting member, or being contaminated by an uncovered used cannula portion of a catheter insertion needle.

Generally, other than acceptance of the type of operation offered by such devices, commercial viability is dependent upon manufacturing cost. Purchase decisions in the area in which these devices are used are very cost sensitive. If gains in either improvement in safety or in labor savings are not found to make a device sufficiently competitive with contemporary items currently on the market, those devices are usually not found to be commercially viable.

An example of a needle protecting catheter insertion device is found in U.S. Pat. No. 4,762,516 issued to Ronald B. Luther, et al. (Luther) on Aug. 9, 1988. An I.V. catheter related product has been generated based upon the disclosure of Luther and is currently being manufactured and distributed by a large international medical products company. The device of Luther discloses an assembly having an elongated housing which mounts a catheter insertion needle. A needle guard is slideably affixed to the housing such that when the housing and needle are retracted relative to the needle guard, the needle guard covers and protects the needle and is permanently locked in place to the housing. Specifically a tab is taught and claimed as an appurtenance against which force is exerted while retracting the housing to withdraw the needle.

This process of retracting a catheter insertion needle from a catheter requires processes which are somewhat different from earlier used catheter inserters having no inherent safety features. In procedures associated with earlier used catheter inserters, a hub or other portion of the catheter is generally stabilized by one hand of an attending technician while the other hand is used to withdraw the catheter insertion needle from the insertion site. For those trained to perform catheter insertions by the earlier used catheter inserters, a passive safety device should require no additional or different procedural steps.

BRIEF SUMMARY AND OBJECTS OF THE INVENTION

In brief summary, this novel invention alleviates all of the known problems related to providing a passively activated, low-cost, whole needle sheltering catheter insertion needle safety device.

To provide a passively activated catheter insertion safety device, a needle covering shield is releasibly affixed to a proximal portion of a catheter assembly such that the catheter may simply be stabilized and an associated catheter insertion needle assembly (as done with earlier catheter inserters without inherent safety features) is withdrawn as simply performed with the earlier catheter inserters. Once the insertion needle is fully withdrawn and locked within the shield, a mechanical sensor and actuator releases the shield (and catheter insertion needle and an associated handle) from the catheter without requiring any other action on the part of an attending technician.

Accordingly, it is a primary object to provide a passively activated safety system used for catheter insertion, said system comprising:

- a catheter assembly comprising a catheter and a hub proximally affixed thereto, the hub comprising an attachable fitting, an appurtenance used for displacing the catheter relative to the needle and stabilizing the catheter assembly during withdrawal of a catheter insertion needle and a catch whereby the catheter assembly is securely, but releasably, affixed to a needle shield;
- the catheter insertion needle, slidably disposed within the catheter and used to facilitate inserting the catheter into a patient, but removed thereafter, leaving the inserted catheter in place, the needle comprising a distal end having a sharpened tip and a proximal end for connecting to a needle hub;
- a handle for gripping the device, the handle comprising exterior gripping surfaces, an interiorly disposed slide track and the needle hub medially disposed within and aligned with the slide track;
- the needle shield slidably engaged on a proximal end to said handle in line with the insertion needle, the shield comprising a hollow interior and a length adequate to contain the insertion needle;
- the needle shield further comprising a latching part having a latch which firmly joins the shield to the catheter assembly via the catch, a mechanical sensor and actuator which detects full displacement of the catheter insertion needle into protective cover of the needle shield and which passively releases the latch from the catch and therefore the catheter assembly from the catheter insertion needle, the handle and the needle shield when such full displacement occurs; and
- a lock which assures the shield is retained in protective engagement about the needle and needle tip upon release of the catheter assembly from the catheter insertion needle, the handle and the needle shield.

Likewise, it is an object to provide-a passively activated shielding apparatus for protective safety of a catheter insertion-needle, the apparatus comprising:

- an elongated housing comprising externally accessible sidewalls which are configured for use as handles, the housing further comprising an inwardly disposed surface and a medially disposed catheter insertion-needle hub raised from the surface upon a stem, the surface defining a slide track for guiding an elongated, hollow needle guard therein;
- the catheter insertion-needle affixed on one end to the needle hub and projecting distally to a sharpened tip in alignment with the slide track;
- the elongated, hollow needle guard disposed about at least a portion of the catheter insertion-needle and engaged inside the surface along the track to slide from a first position where the needle guard is displaced away from the sharpened needle tip such that the catheter insertion-needle tip is bared for insertion into a patient to a second position where the needle tip is covered and protected by the needle guard, the needle guard comprising a releasible latching assembly for a catheter hub and a slot wherethrough a latching part is disposed to communicate with the catheter insertion-needle when the catheter insertion-needle is unprotected by the needle guard;
- a catheter assembly comprising an elongated catheter, sized to be disposed about the catheter insertion-needle for hypodermic insertion, and a luer type hub whereby the catheter is aligned with and securely, but releasibly, affixed to the latching assembly, the hub comprising a raised proximal portion, having an edge which acts as a catch, and a tab for displacing the catheter assembly relative to the elongate housing;
- the latching part, disposed to fit through the slot to thereby provide an external segment, which communicates with the proximal edge portion of the luer type hub to form the latching assembly, and an internal segment which is disposed to communicate with the catheter insertion-needle, the external segment comprising a latch for the catch and the internal segment comprising a hole through which the catheter insertion-needle passes and by which the catheter insertion-needle maintains sufficient stress upon the latching part to cause the latch, and catch to remain securely affixed until the catheter insertion-needle is displaced sufficiently far within the needle guard for safety to the second position whereat the catheter insertion-needle and sharpened needle tip clear the hole relieving the stress on the latching part which responsively releases the latch from the catch permitting the housing, guard, catheter insertion-needle and latching part to be passively displaced away from the catheter assembly by the act of simply pulling the catheter insertion-needle out of, the catheter assembly; and
- a lock which unreleasibly secures the catheter insertion-needle inside the needle guard for safety.

Very importantly, it is a fundamental object to provide a method for passively activating a safety shield while withdrawing a catheter insertion-needle from an inserted catheter comprising the steps of:

providing:
- an elongated housing comprising externally accessible finger grips, the housing further comprising a medially disposed catheter insertion-needle hub and a slide track for guiding an elongated, hollow needle guard therein;
- the catheter insertion-needle affixed on one end to the needle hub and projecting distally to a sharpened tip in alignment with the slide track;
- the elongated, hollow needle guard engaged to slide linearly along the track from a first position to a second position, the needle guard comprising a releasible fitting for a catheter hub and a slot wherethrough a latching part is disposed for communicating with the catheter insertion-needle;
- a catheter assembly comprising an elongated catheter, sized to be disposed about the catheter insertion-needle for insertion, and a luer type hub whereby the catheter is aligned with and securely, but releasibly, affixed to the fitting, the luer type hub comprising a raised edge which acts as a catch, and a digitally accessible member;
- the latching part, disposed to fit through the slot to thereby provide an external segment, which communicates with the raised edge, and an internal segment which is disposed to communicate with the catheter insertion-needle, the external segment comprising a latch for the catch and the internal segment comprising a hole through which the catheter insertion-needle passes and by which the catheter insertion-needle maintains sufficient stress upon the latching part to cause the latch and catch to remain securely affixed; and
- a lock which unreleasibly secures the catheter insertion-needle inside the needle guard for safety;

inserting the catheter insertion-needle and catheter into a patient;

assuring the catheter is properly positioned at a predetermined site;

while applying restraining force to assure the catheter stays at the predetermined site, applying proximally directed force at the finger grips thereby displacing the catheter insertion-needle proximally, relative to the stationary catheter, into the needle guard until the catheter insertion-needle is disposed, sufficiently far within the needle guard to protect the needle tip, at the second position and to clear the hole relieving the stress on the latching part which responsively releases the latch from the catch permitting the luer type hub to be separated from the fitting allowing the housing, guard, catheter insertion-needle and latching part to be passively displaced away from the catheter assembly by the act of simply pulling the catheter insertion-needle out of the catheter assembly; and concurrently, within the applying step, unreleasibly locking the needle guard relative to the housing to assure needle safety.

These and other objects and features of the present invention will be apparent from the detailed description taken with reference to accompanying drawings.

DETAILED DESCRIPTION OF THE ILLUSTRATED EMBODIMENTS

In this description, the term "proximal" is generally used to indicate relative nearness of a referenced item to a prospective user of a device, unless otherwise specified. The term "distal" is similarly used to indicate relative remoteness. The terms "passive" and "passively activated" are used as descriptors for a function which occurs substantially subliminally or indiscernibly as a result of, and usually concurrent with, an action which performs a different function. As an example, a passively activated safety mechanism for a catheter insertion needle is a safety mechanism which is subliminally activated at a predetermined point in a catheter insertion procedure without cognizance of or performance of any additional steps being required other than those steps which are necessary for a non-safety device when used to insert a catheter, then withdraw and separate a catheter insertion needle.

Figure 1:
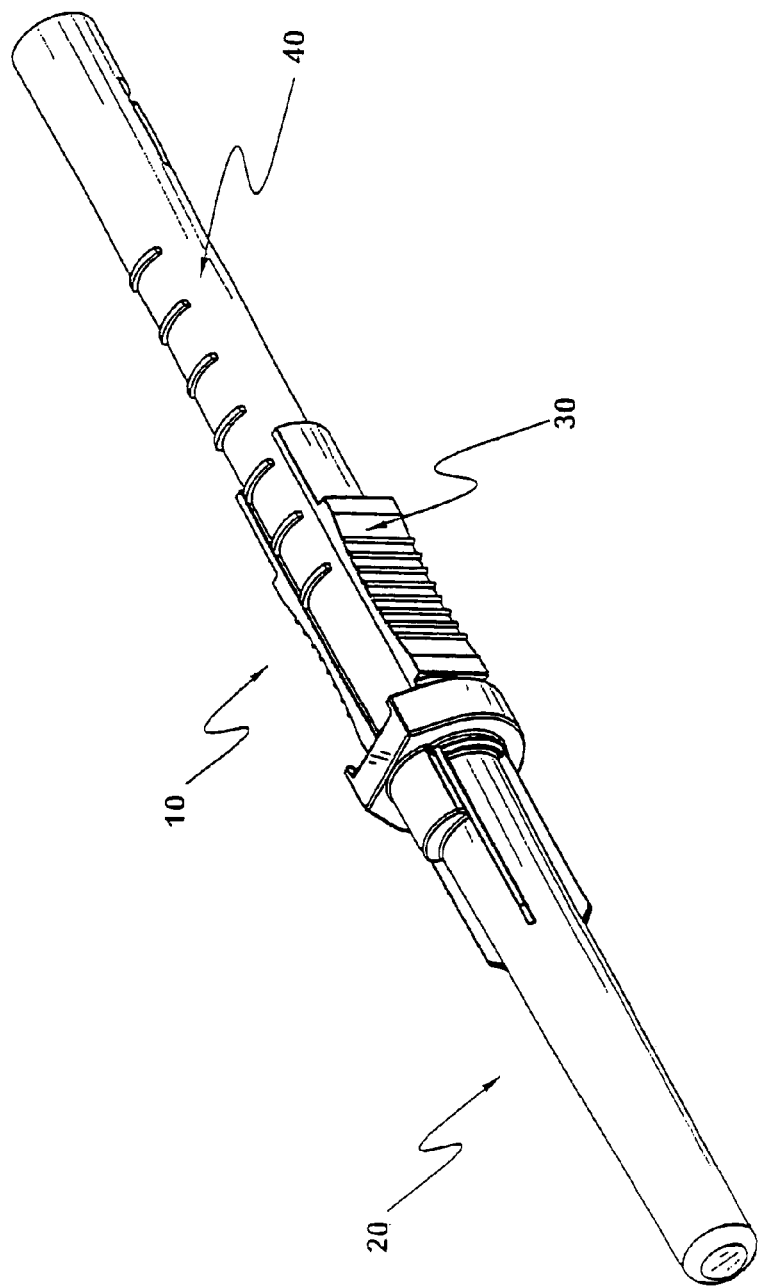
FIG. 1 is a perspective of one embodiment of a passively activated, fully needle sheltering catheter insertion needle safety device as transported prior to use.

As seen in FIG. 1, a first embodiment of the invention is seen as device 10 with an associated needle cover 20. As configured in FIG. 1, parts of device 10 which should be kept free from damage or contamination are protected by cover 20 in transport, storage and as otherwise handled prior to use. As is seen before cover 20 is removed, device 10 comprises an elongated housing 30 and a needle shield 40. As better seen in FIG. 2, cover 20 encloses a distally disposed catheter assembly 50, a catheter insertion needle 60 and a clip or latching part 70.

Cover 20 has a substantially hollow, cylindrically shaped portion 72, closed at a distal end 74. On a proximal end 76, cover 20 is formed to be snugly, but releasibly affixed to handle 30. Cover 20 may be made from a number of synthetic resinous materials, but is preferably injection molded from polypropylene.

Figure 3:
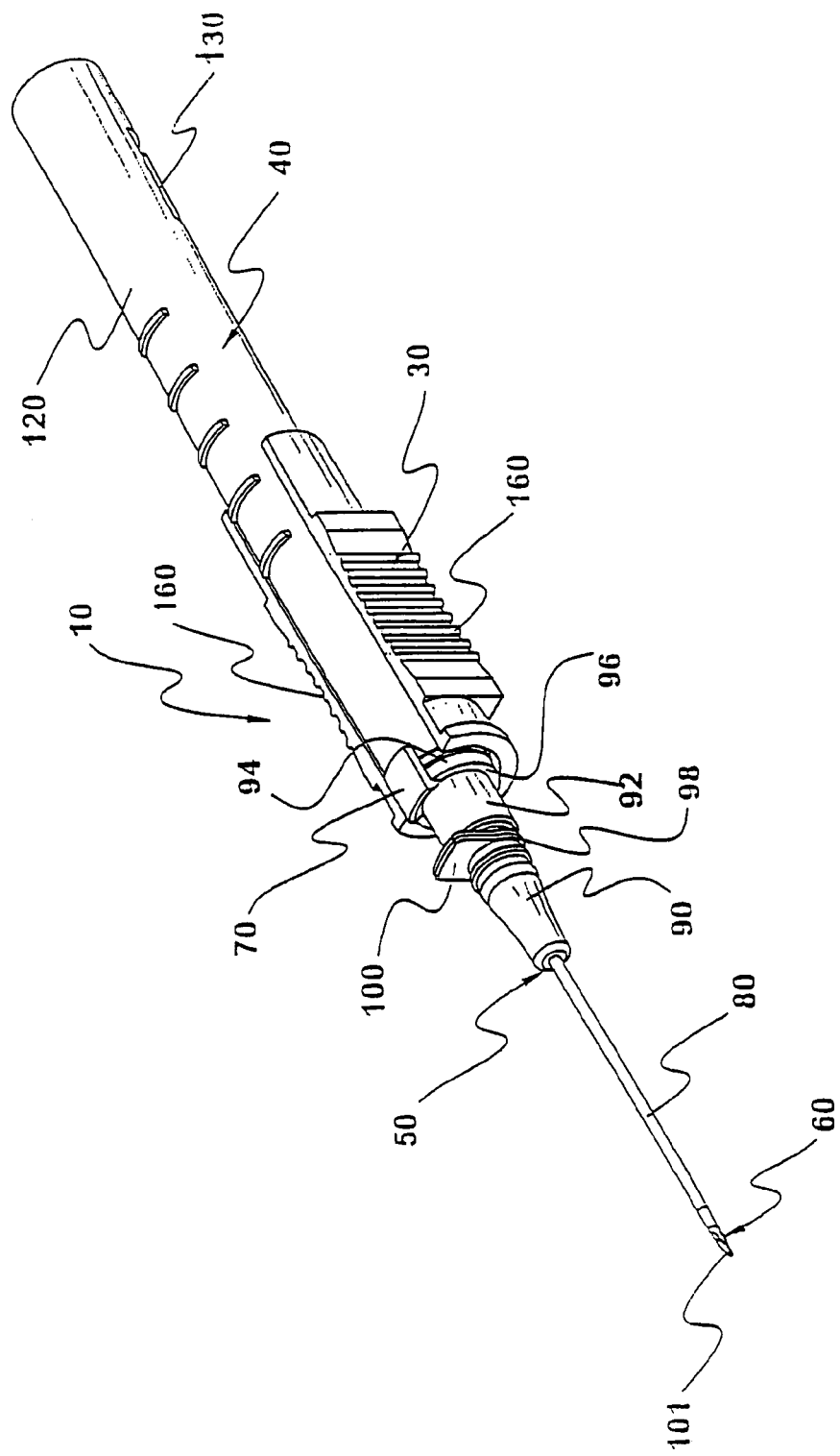
FIG. 3 is a perspective of the device seen in FIG. 1 with a needle cover removed.
Figure 11:
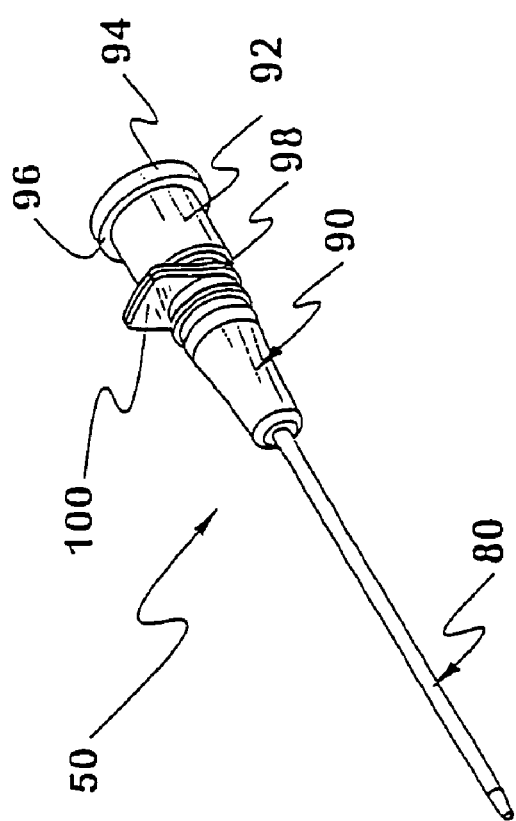
FIG. 11 is a perspective of a catheter assembly associated with the catheter.

Attention is now drawn to FIG. 3 where device 10 is seen with cover 20 removed therefrom, and to FIG. 11 where catheter assembly 50 is seen as a separate part. As may be seen in FIG. 11, catheter assembly 50 is assembled with a catheter 80 securely affixed to a catheter hub 90. Catheter hub 90 has a proximally disposed fitting 92 which abruptly ends at a raised rim 94 which is truncated distally at an edge 96. While rim 94 and edge 96 may be made in many forms, it is important that they be formed to provide a catch function which is disclosed in detail hereafter. Also prominently affixed to a medically disposed exterior portion 98, of hub 90, is a tab 100. Tab 100 also may have many forms within the scope of the invention, but it is important that an appurtenance, which in this case is provided by tab 100, be provided for digitary access so that catheter 50 can be facilely displaced distally during catheter emplacement and so that catheter 50 can be held to resist further displacement when the catheter insertion needle is widrawn.

Referring, again, to FIG. 3, device 10 has needle 60 (and an associated sharpened tip 101) and catheter 80 bared for an insertion procedure. Catheter assembly 50 is securely affixed to needle shield 40 by an interlocking connection made between latching part 70 and edge 96.

Figure 16:
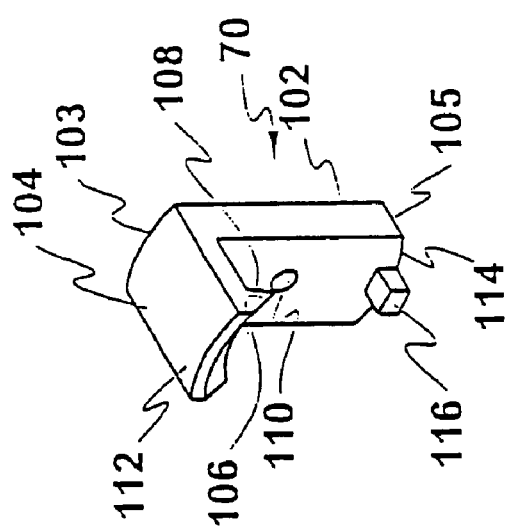
FIG. 16 is a perspective of a latching part which is used to releasibly affix the catheter assembly to the separable portion of the device.

A more detailed view of latching part 70 is seen in FIG. 16. Latching part 70 has a proximally disposed upright member 102 which terminates superiorly at end 103 with a transversely and distally extending beam 104 and inferiorly at end 105. Beam 104 abruptly ends with a downwardly extending flattened tooth 106 which provides a proximally facing latch 108. Upright member 102 also has a through hole 110 which is sized and disposed first to conformably permit catheter insertion needle 60 to slide therethrough and second to hold latch 108 in a secure connection with edge 96 as long as catheter insertion needle 60 remains in through hole 110. Beam 104 has an exterior surface 112 and end 105 has an inferior surface 114. Each surface, 112 and 114, has a curvature which conforms with interior radii of curvature of needle shield 40. Also extending distally from member 102 at surface 114 is a key-block 116, which is used to provide stability to latching part 70 after release by retraction of, insertion needle 60.

Note in FIG. 3 that handle 30 is disposed in close proximity to tab 100, thereby permitting facile distal displacement of catheter assembly 50 relative to handle 30, a procedure which is commonly practiced to extend catheter 80 beyond needle tip 101 once a vein or artery has been entered. Once catheter 80 is properly positioned within the vein or artery, it is also common practice to remove needle 60 therefrom. In devices without a shield or other safety apparatus to protect needle 60 and sharpened tip 101, needle 60 is removed and resulting safety from injury from needle 60 and sharpened tip 101 is dependent upon careful handling and disposition, perhaps into a sharps container. It is common knowledge that many needlestick injuries have occurred before needle disposition. Even so, the procedure of removing a needle from a catheter is well inserviced worldwide and, for this reason, there is a strong need for a device which passively shrouds a shield about the needle and associated needle tip.

Figure 14:
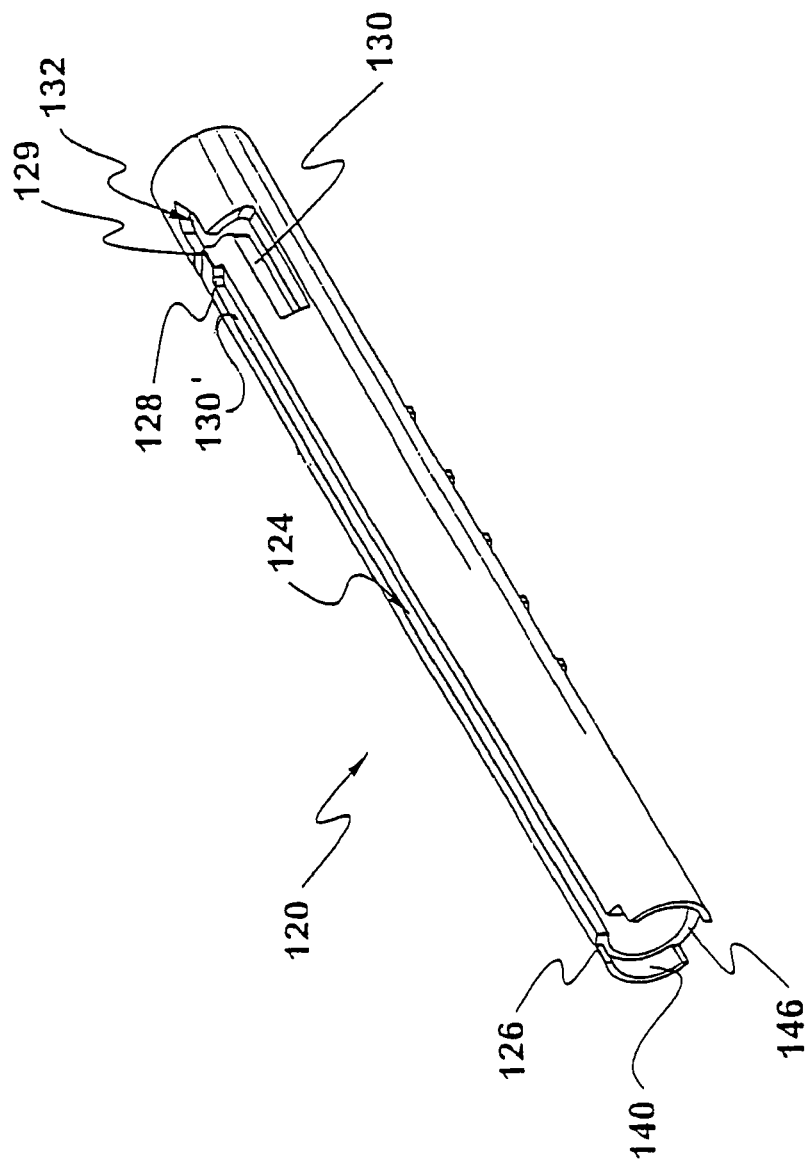
FIG. 14 is a perspective of the shield used to surround and protect the catheter insertion needle when withdrawn from the catheter.
Figure 15:
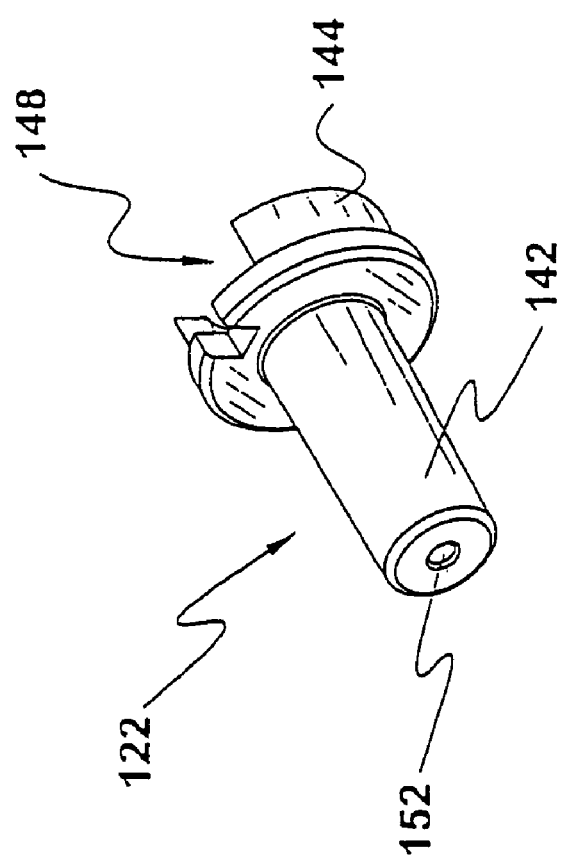
FIG. 15 is a perspective of an interfacing part disposed between the shield and the catheter assembly.

In this embodiment, a proximal portion 120 of needle shield 40 is an elongated, substantially hollow cylinder. Proximal portion 120 is securely affixed to a nose section 122 seen in FIGS. 8 and 15 to form a whole needle shield 40. As seen in FIG. 14, proximal portion 120 is rotated 180 degrees about the long axis of portion 120 to provide a clear view of an elongated slit 124 which is open at a distal end 126 and closed at a proximal end 128. Closure at the proximal end 128 is accomplished by a separable juncture 129 of a pair of opposing arms 130 and 130'. More proximally, portion 120 has a opening 132 in line with slit 124 and juncture 129. For reasons disclosed hereafter, it is important that arms 130 and 130' be readily separable when a part is displaced between them via slit 124 toward opening 132, but substantially inseparable should an attempt be made to displace that part from opening 132 toward slit 124.

As seen in FIG. 14, distally disposed near slit end 126 is a female fitting 140 whereby nose section 122 is connected to portion 120 to form a whole needle shield 40. Of course, for nose section 122 to be properly joined to portion 120, portion 120 must be rotated 180 degrees about its long axis. Nose section 122 has a nose portion 142 which is sized and shaped to provide a stabilizing connection between needle shield 40 and catheter assembly 50. Proximally disposed relative to nose portion 142 is a male fitting 144 which is sized and shaped to make a secure joint with fitting 140. Note, in FIG. 14, that portion 120 has an open flute 146 which coincides with an open flute 148 of nose section 122 to form a slot 150, see FIG. 8, wherethrough member 102 of latching part 70 communicates between needle 60 and edge 96 to releasibly, but securely join needle shield 40 to catheter assembly 50. Nose section 122 has a through hole 152 which is sized to permit needle 60 to facilely glide therethrough while constraining transverse motion of needle 60 during withdrawal to stabilize needle 60 relative to a mechanical sensor function performed by hole 110 in latching part 70.

Figure 12:
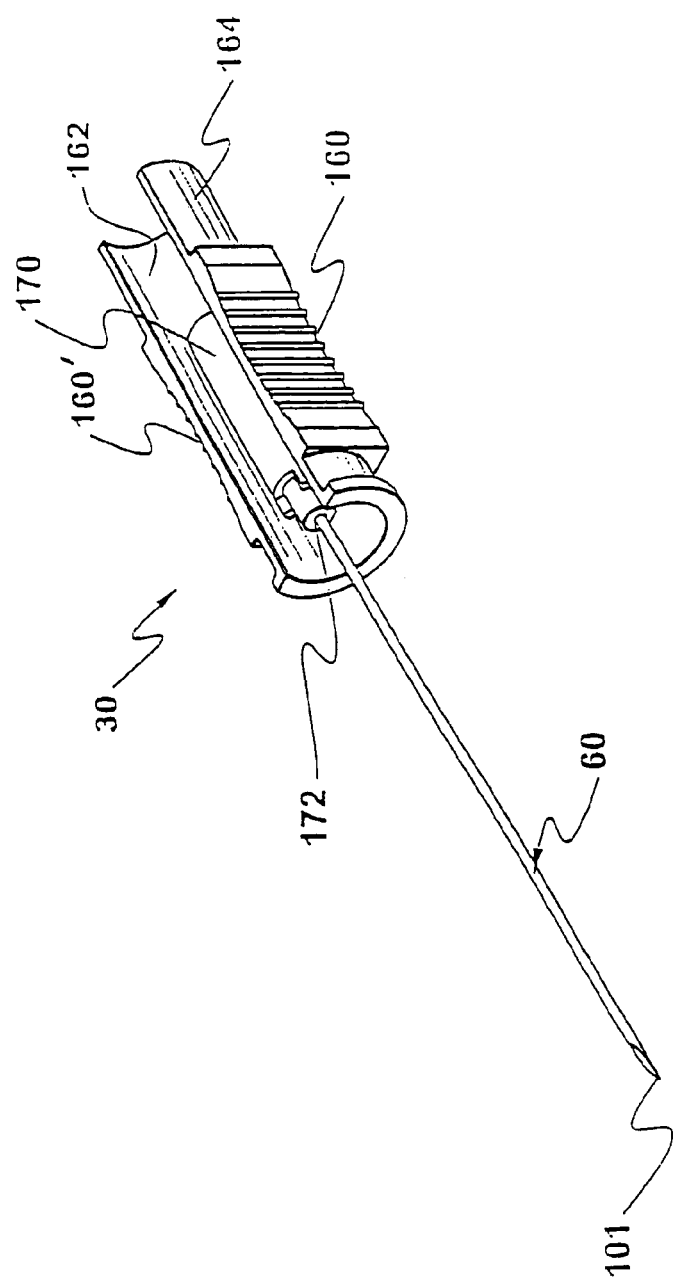
FIG. 12 is a perspective of a handle assembly which has a hub for mounting the catheter insertion needle.

As seen in FIG. 3, handle 30 is an elongated housing having a pair of exteriorly disposed sidewalls which act as gripping surfaces 160 and 160' for facile handling of device 10. Handle 30 is seen in FIG. 12 free from needle shield 40 and catheter assembly 50. Though, within the scope of the instant invention disclosed herein, handle 30 may be differently configured, handle 30 has an open cylindrically shaped internally disposed surface 162 which is sized and shaped to form a track structure 164 wherein portion 120 of needle shield 40 glides distally and proximally.

Figure 2:
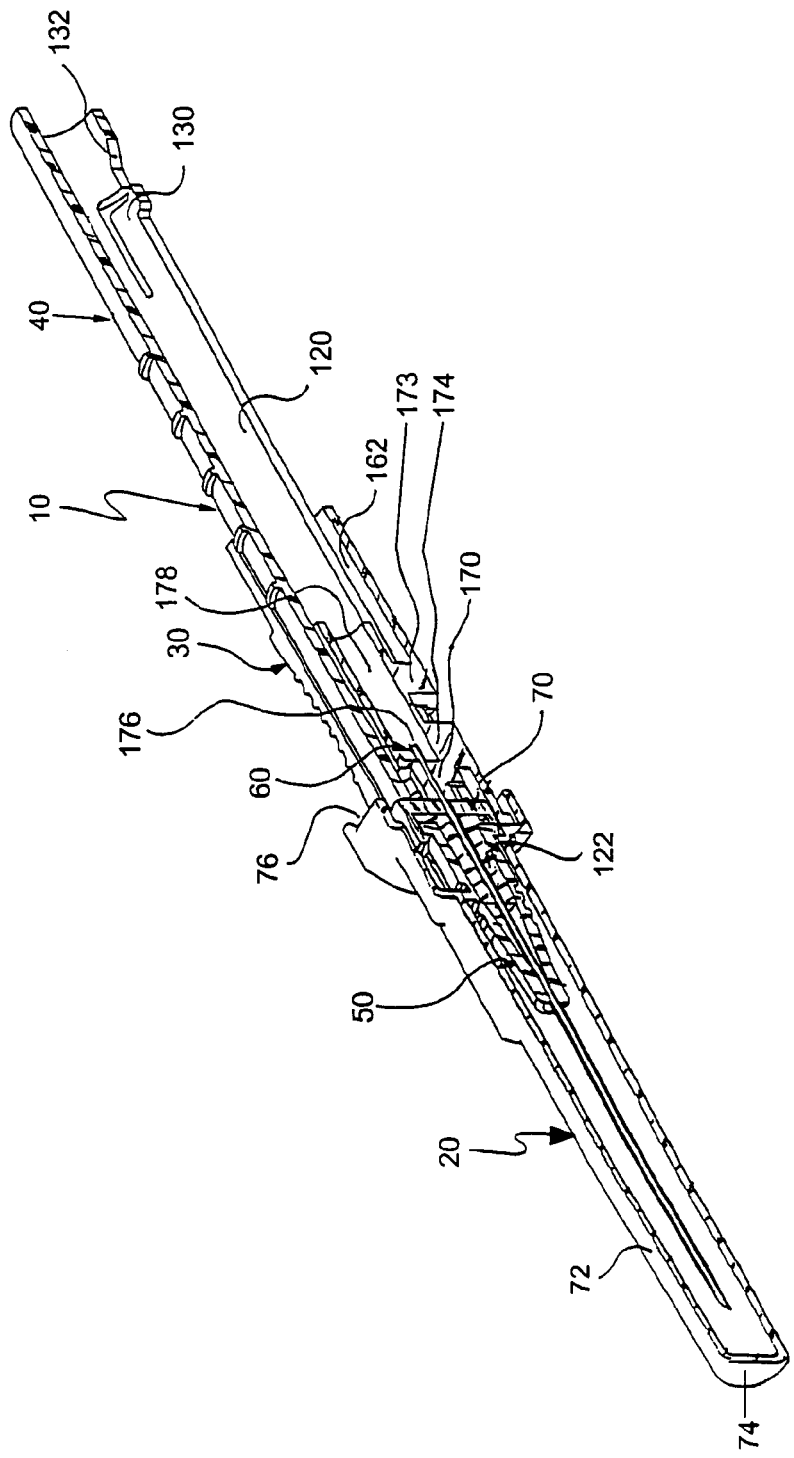
FIG. 2 is a cross section of the device seen in FIG. 1.

Medially disposed within surrounding surface 162 is a needle hub 170. Hub 170 has a medially disposed bore hole 172 in which insertion needle 60 is securely affixed by process which are well known in the art of affixing medical needles in hubs. As seen in FIG. 2, hub 170 is displaced from surface 162 by a pair of stems 173 and 174. Proximally disposed from a proximal end 176 of needle 60, hub 170 comprises a cylindrical cavity 178 used as an indicator of "blood flash" a common signal of successful catheter insertion. A plug (not shown) is commonly applied to a proximal end of cavity 178. Such plugs, well known in the art of making catheter inserters, are selective filters which are gas (air) permeable, but which are liquid impermeable to fully contain blood flowing therein.

Handle 30 may be made from a wide variety of synthetic resinous materials, but care should be taken to select materials which are clear for a transparent view of hub 170. Further, the selected material should provide either for adhesion or a reliable press fit of needle 60. Similarly, needle shield 40 may be made from a wide variety of synthetic resinous materials (preferably by injection molding), but should also be transparent to provide a clear view-of hub 170. Such a material may be polystyrene.

Figure 13:
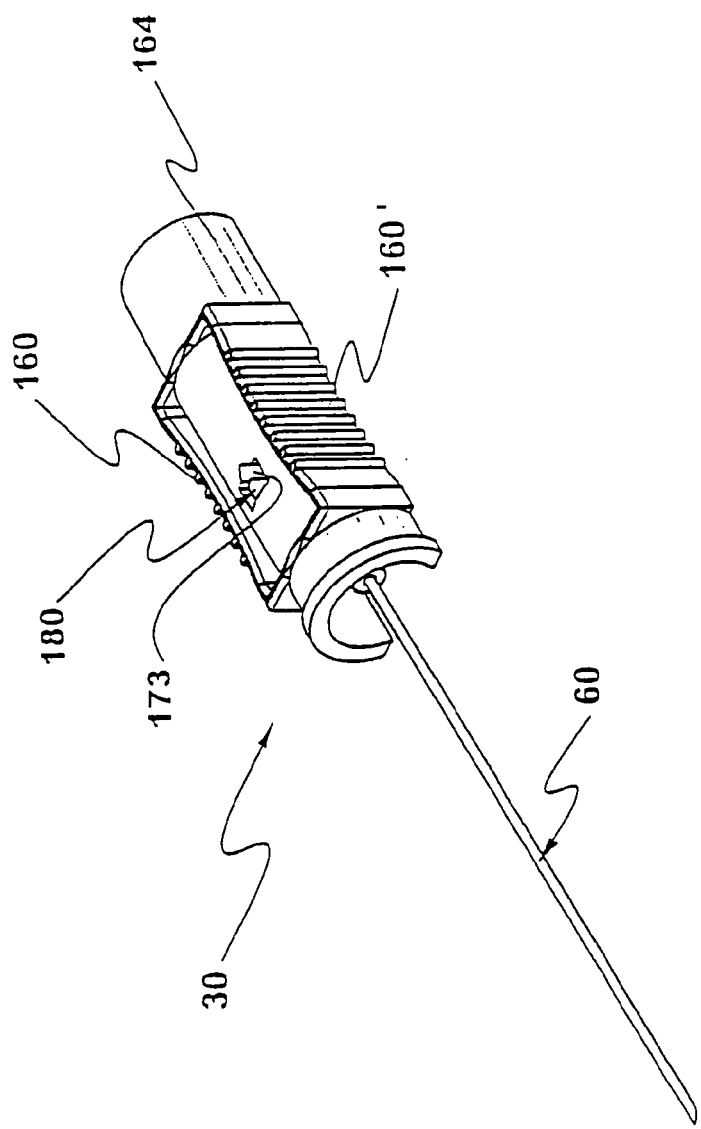
FIG. 13 is a perspective of the assembly as seen in FIG. 12, but rotated to show parts hidden in FIG. 12.

Attention is now drawn to FIG. 13 wherein handle 30 is rotated 180 degrees about the long axis of needle 60 relative to the view of handle 30 seen in FIG. 12 such that-a through hole 180 in track structure 164 may be seen. Hole 180 is disposed between stems 173 and 174 (see FIGS. 2 and 8), defining a size of stem 173 which fits within opening 132 (see FIG. 14). In this manner, when handle 30 is displaced proximally relative to needle shield 40 until stem 173 is disposed in opening 132, juncture 129 is opened and closed during the proximal displacement, and then remains securely closed to distal displacement, thereby forming a secure lock. Thus, needle 60, once contained within needle shield 40 is unreleasibly held for safety therein.

Figure 4:
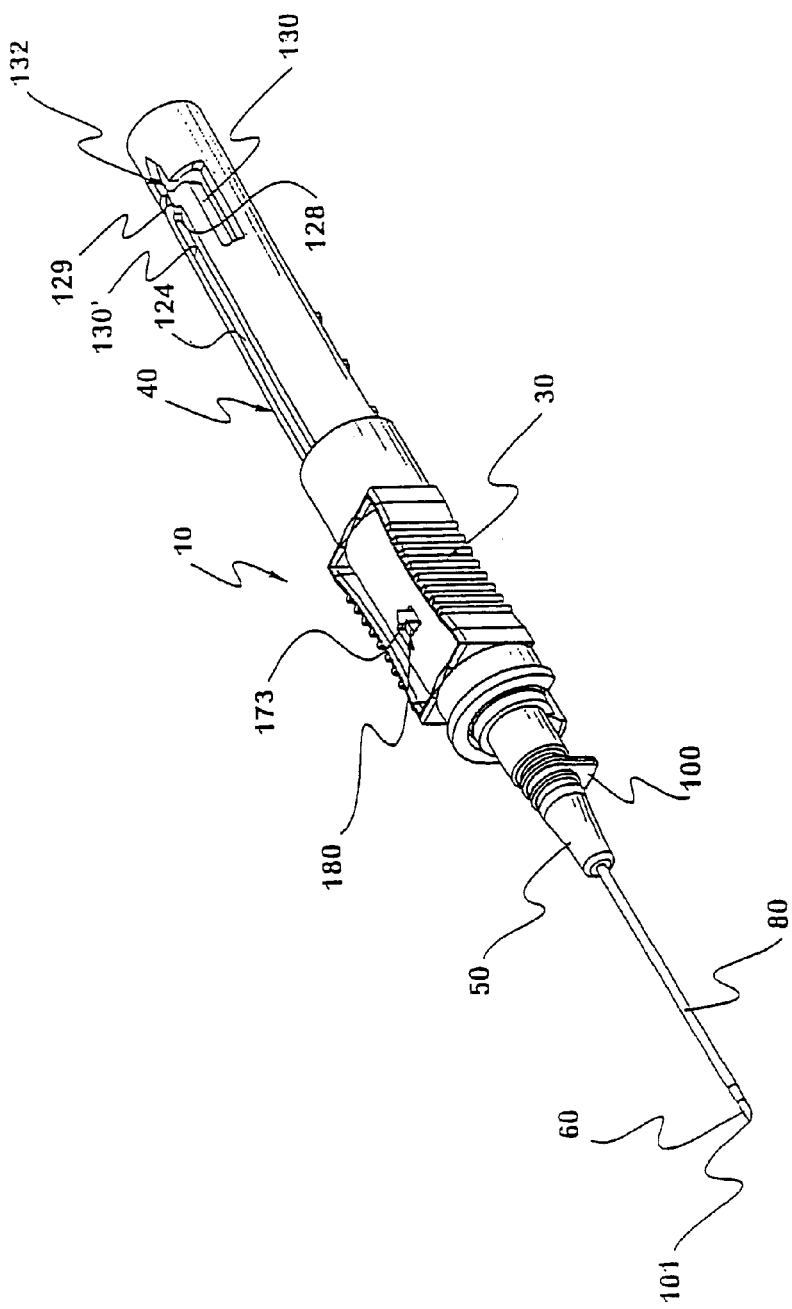
FIG. 4 is a perspective of the device as seen in FIG. 3, but rotated to show parts hidden in FIG. 3.
Figure 7:
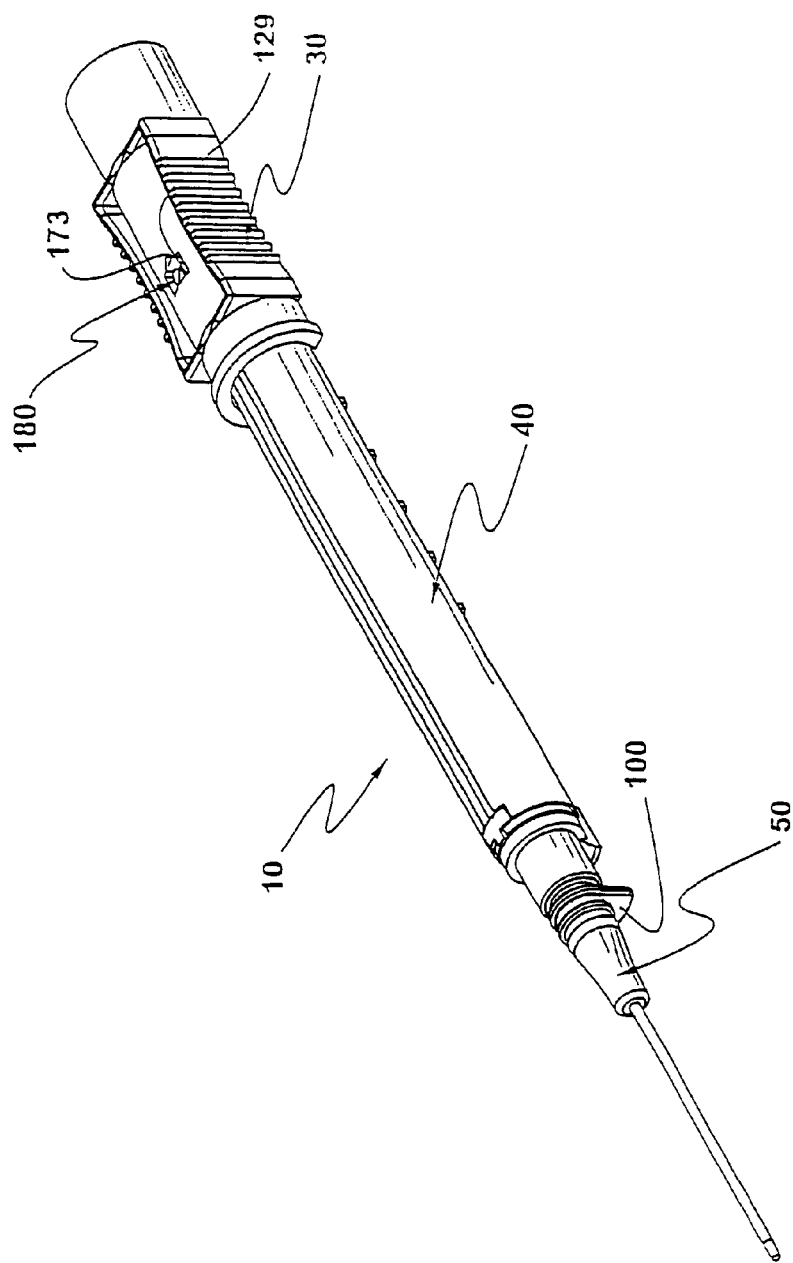
FIG. 7 is a perspective of the device as seen in FIG. 6, but rotated to show parts hidden in FIG. 6.
Figure 8:
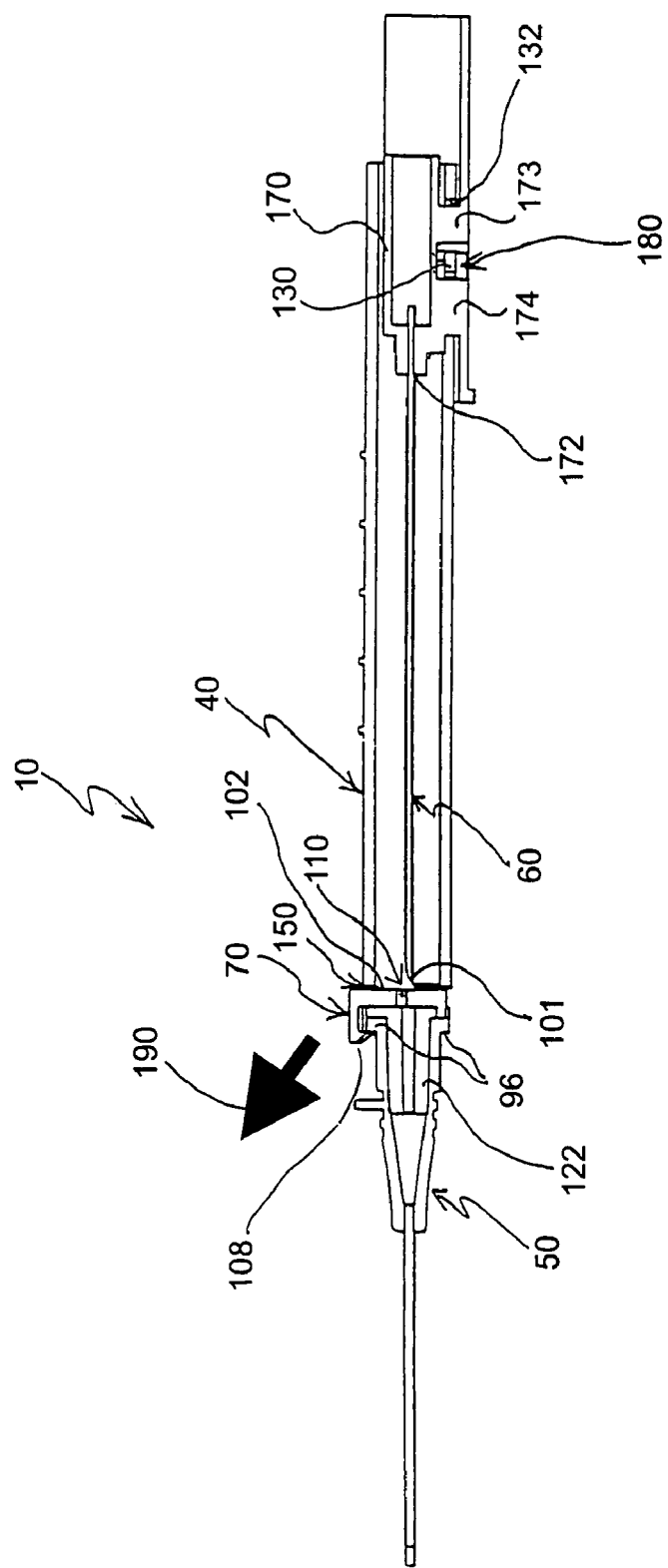
FIG. 8 is a cross section of the device as seen in FIG. 6.
Figure 9:
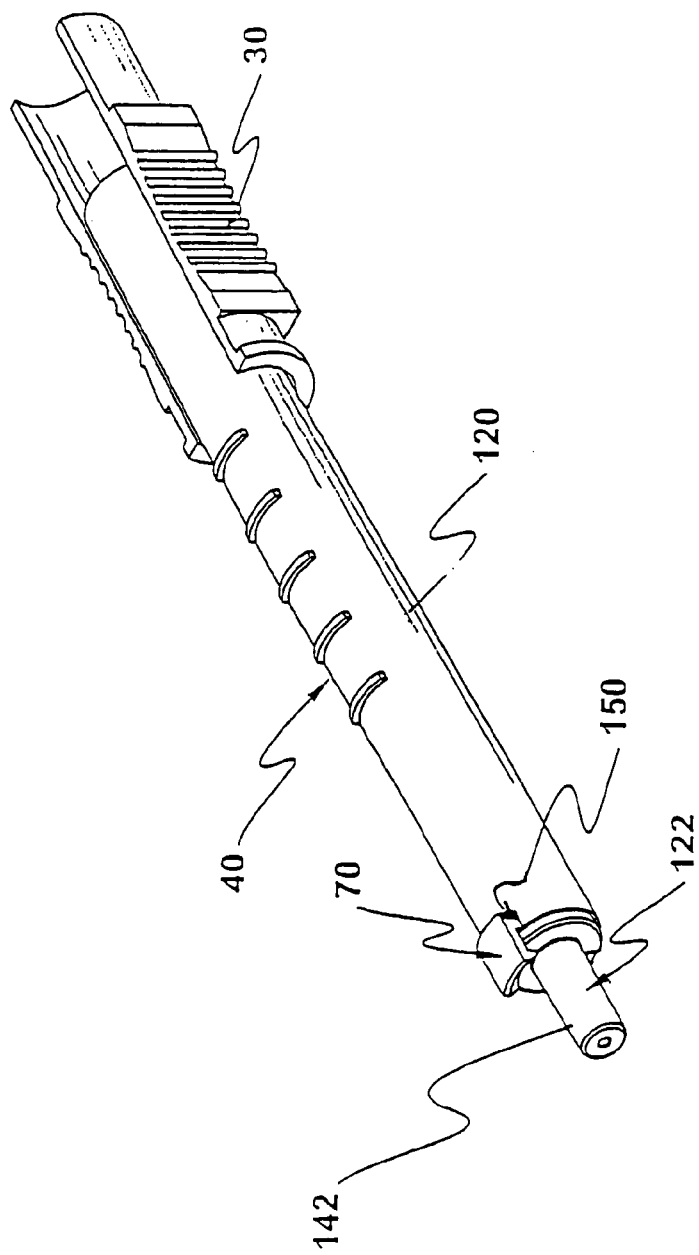
FIG. 9 is a perspective of a separated portion of the device seen in FIG. 6, after being separated and displaced from the catheter.
Figure 10:
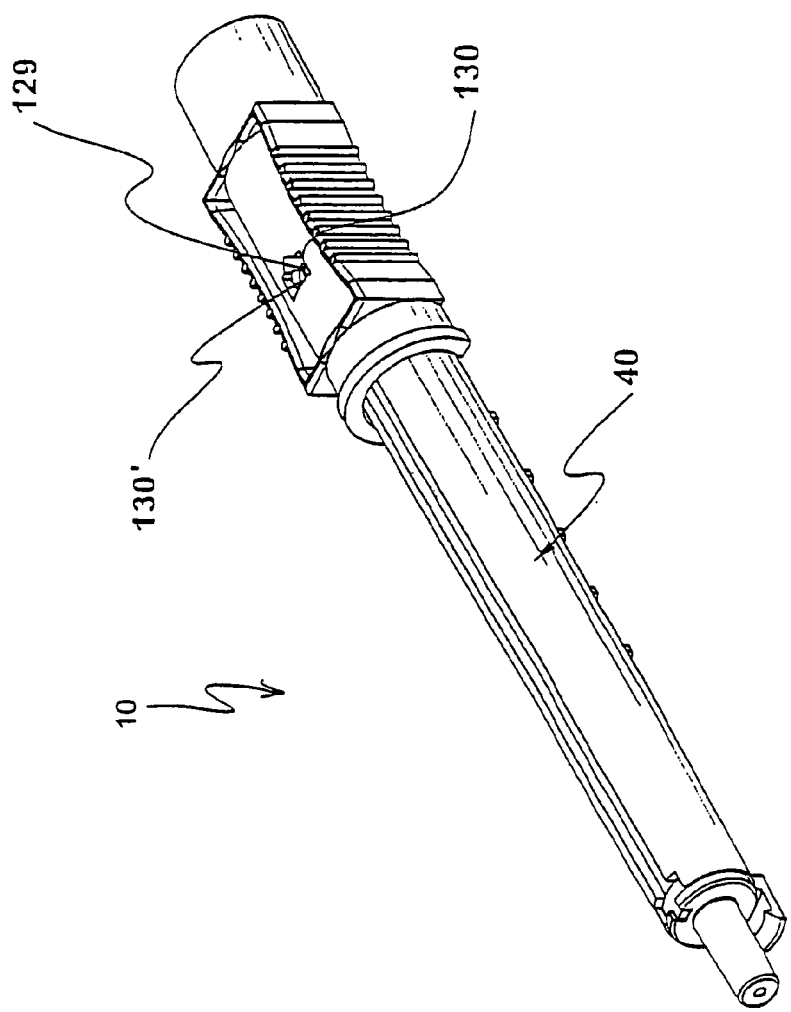
FIG. 10 is a perspective of the portion as seen in FIG. 9, but rotated to show parts hidden in FIG. 9.

Critical, to the instant invention herein disclosed, is the operation of device 10. As seen in FIG. 4, stem 173 is disposed just proximal of hole 180. (Device 10 is inverted from normal use disposition for visual access to slit 124, arms 130 and 130', juncture 129 and opening 132 of needle shield 40.) References to FIGS. 4, 7 and 8 are recommended for visualization of parts involved in activation of an unreleasible lock for this embodiment.

Device 10 as seen in FIG. 3 ready for catheter 80 insertion. Generally, handle 30 is grasped at finger grips 160 and 160' with a bevel at needle tip 101 slanted proximally upward. Percutaneous insertion is accomplished into a vessel or other catheter target and an appropriate indication thereof is determined consistent with contemporary catheter insertion procedures. Once catheter 80 is inserted, it is common practice to urge catheter 80 distally to a predetermined position, usually, at least, until tip 101 is covered by catheter 80. For this purpose, a facilely accessed structure or appurtenance, such as tab 100 is usually provided. It should be noted that such urging of catheter 80 distally, also, of course, displaces the whole of catheter assembly 50 distally as well as needle shield 40 which is affixed to catheter assembly 50 via latching part 70.

Figure 5:
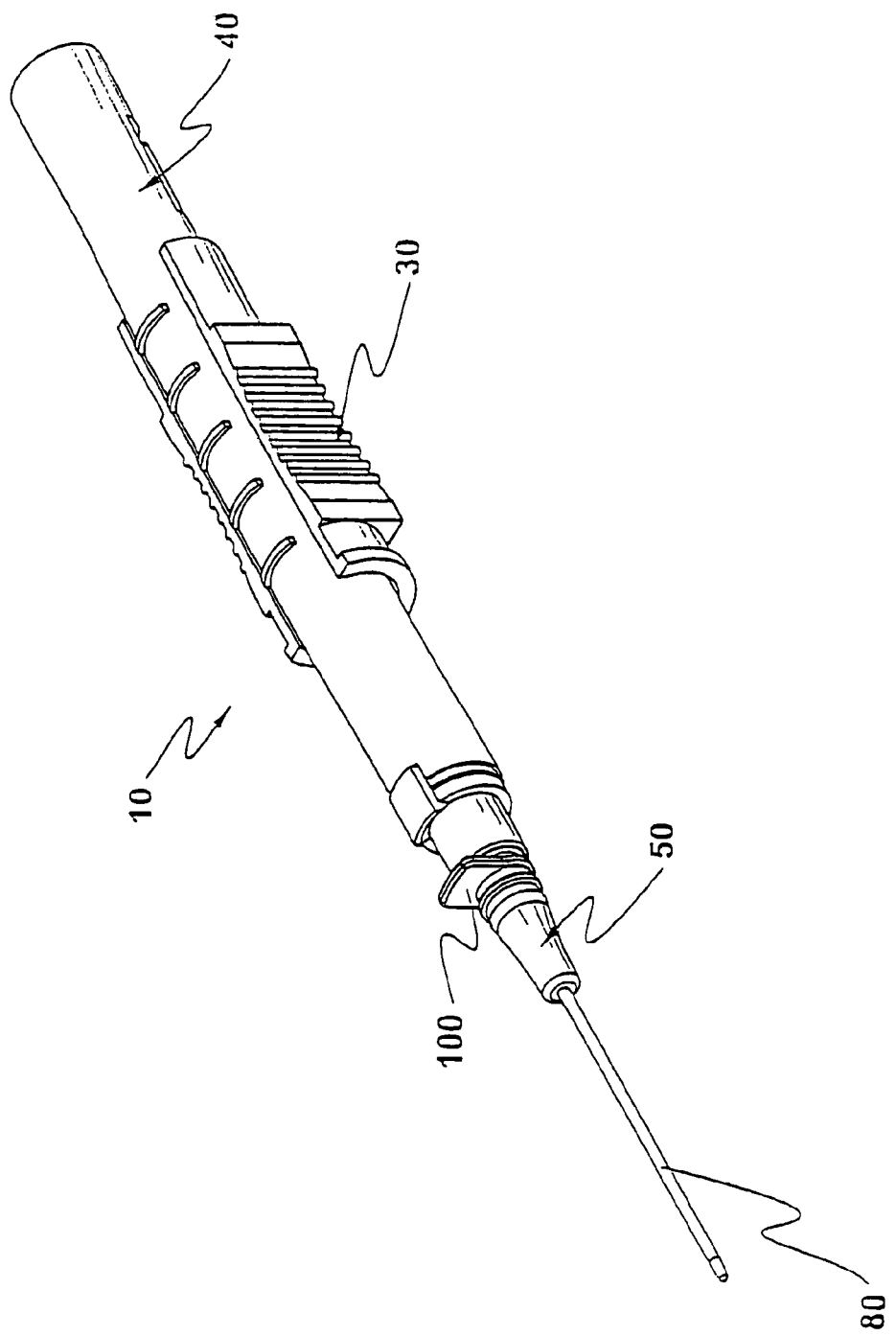
FIG. 5 is a perspective of the device seen in FIG. 3 with a handle displaced to partially withdraw a catheter insertion needle from a distally disposed catheter.
Figure 6:
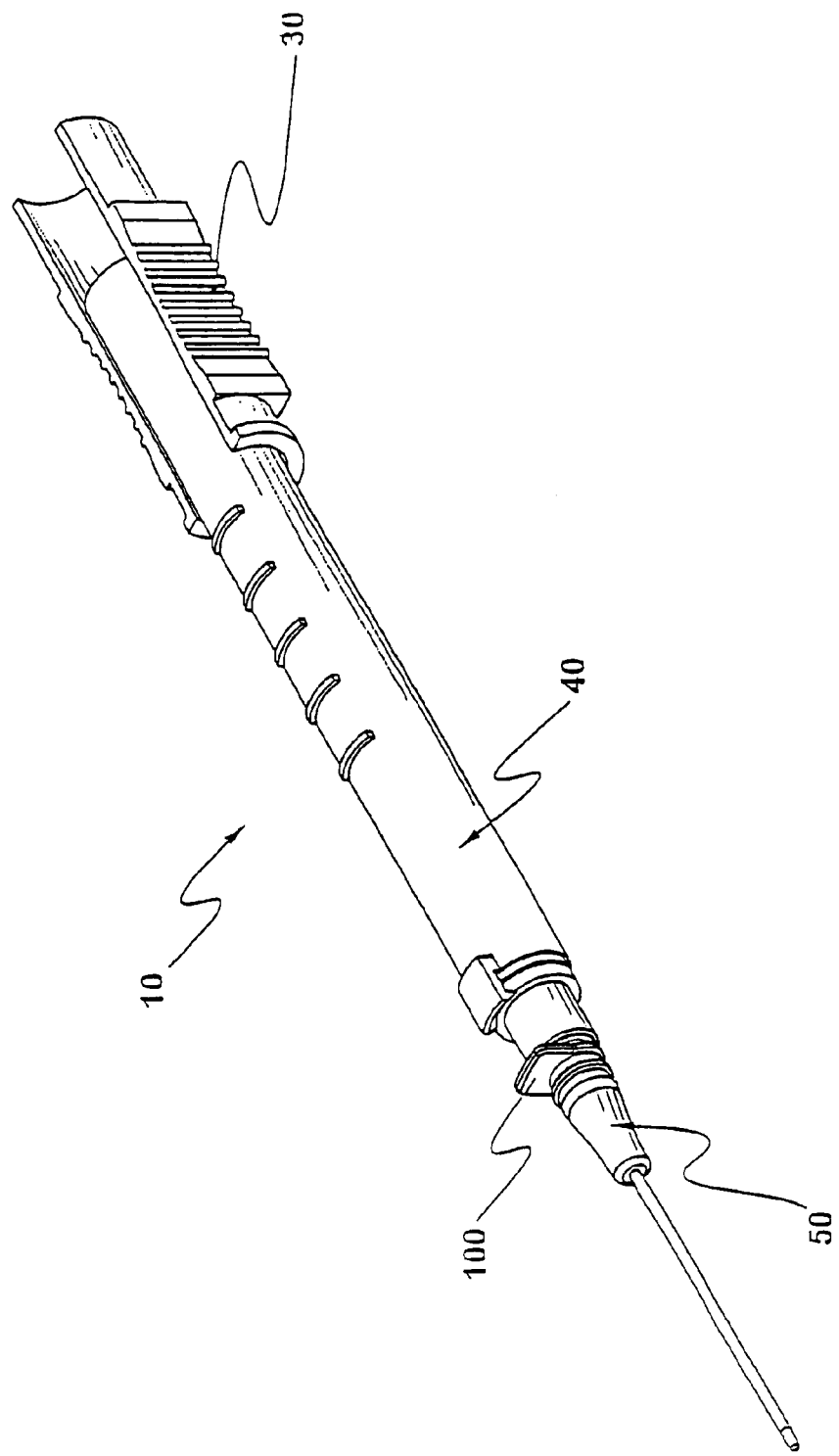
FIG. 6 is a perspective of the device seen in FIG. 5 with the handle further displaced to completely withdraw the catheter insertion needle into safety of a surrounding needle shield.

Once catheter 80 is displaced to the predetermined position, catheter assembly 50 is firmly held against further displacement, usually by pressure applied to the appurtenance (tab 100 in this case), while handle 30 is displaced proximally, as seen in FIG. 5. Note, both catheter assembly 50 and needle shield 40 remain static. Distal displacement of needle shield 40 displaces needle 60 (not seen in FIG. 5) relatively proximally through catheter 80. Device 10 with handle 30 totally proximally displaced is seen in FIGS. 6, 7 and 8. In the inverted view of device 10 seen in FIG. 7, stem 173 is proximally disposed relative to juncture 129 as seen through hole 180. Note also, that stem 173 should be locked behind juncture 129 before needle tip 101 clears through hole 110, as seen in FIG. 8.

Once needle tip 101 clears through hole 110, latching part 70 is released to be pulled upward in the general direction of arrow 190 which frees latch 108 from edge 96, without undue action and therefore passively, to free catheter assembly 50 from catheter insertion needle 60, handle 30 and needle shield 40. The combination of catheter insertion needle 60, handle 30 and needle shield 40 is passively separated for disposal with needle 60 being unreleasibly contained for safety in needle shield 40. As stem 173 must pass through juncture 129, it is important that arms 130 and 130' be flexible and easily laterally displaced so that no undue restrictive force is imposed upon catheter assembly 50 prior to release of latching part 70 and subsequent separation of needle shield 40 from catheter assembly 50.

Reference is made to FIGS. 17–24 wherein another embodiment (specifically device 10') of the present invention is disclosed. Except for a difference in form and function of a needle shield 40' and handle 30' relative to needle shield 40 and handle 30, respectively, device 10' is substantially the same as device 10, seen in FIGS. 1–11 and 16. Methods for initially urging catheter assembly 50 distally and withdrawing and passively separating catheter insertion needle 60, handle 30' and needle shield 40' from catheter assembly 50 are also substantially the same as the method, earlier disclosed, for urging catheter assembly 50 distally and withdrawing and passively separating catheter insertion needle 60, handle 30 and needle shield 40.

Figure 17:
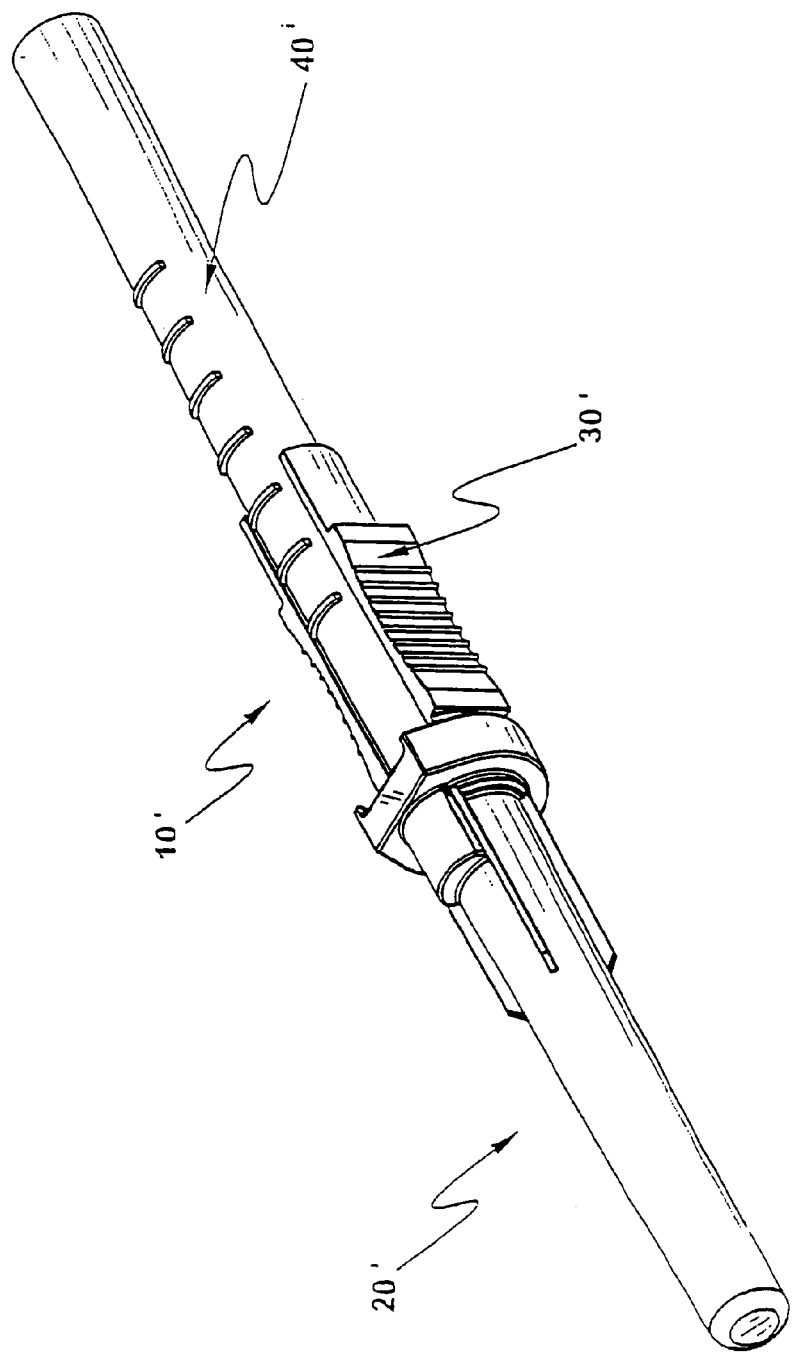
FIG. 17 is a perspective of another embodiment of a passively activated, fully needle sheltering catheter insertion needle safety device as transported prior to use.
Figure 18:
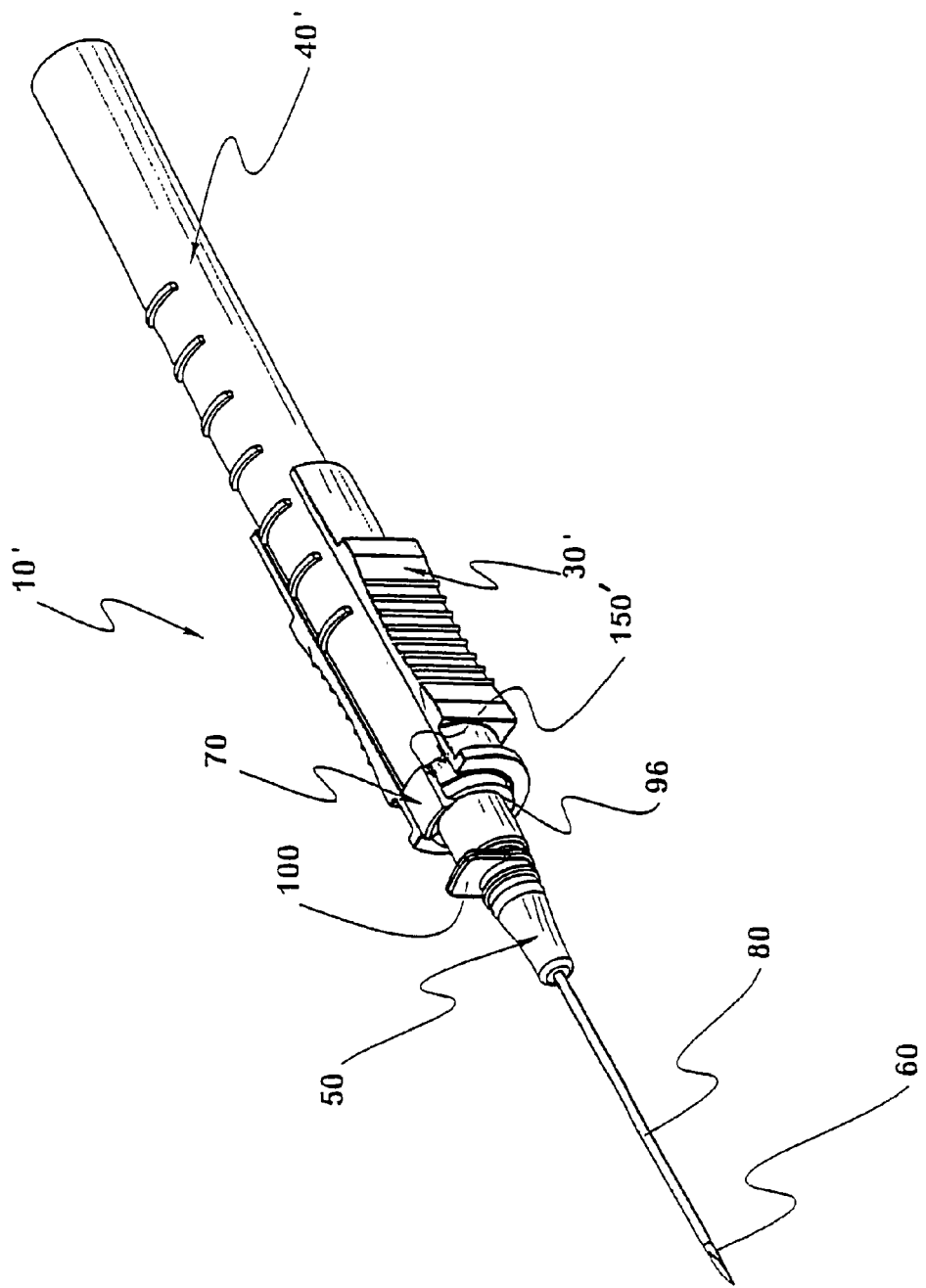
FIG. 18 is a perspective of the device seen in FIG. 17 with a needle cover removed.

Similar to device 10, as seen FIG. 1, device 10' is shown with a cover 20 protectively covering a needle, also numbered 60 for device 10' in FIG. 17. FIG. 18, which is similar to FIG. 3 shows a catheter assembly 50 and needle 60 exposed preparatory to catheter insertion.

Figure 24:
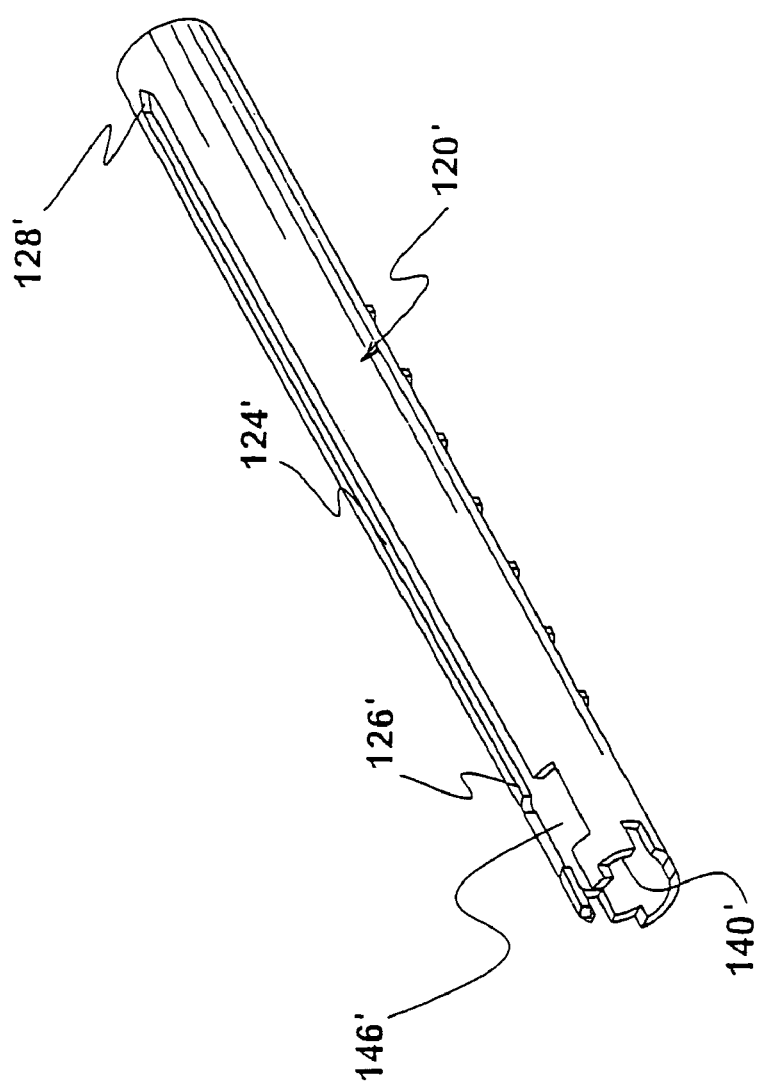
FIG. 24 is a perspective of the shield used to surround and protect the catheter insertion needle when withdrawn from the catheter.

Reference is now made to FIG. 24, wherein a proximal portion 120' of needle shield 40' is seen. In this embodiment, proximal portion 120' of needle shield 40' is an elongated, substantially hollow cylinder. Proximal portion 120' is securely affixed to a nose section 122', seen in FIG. 25, to form a whole needle shield 40'. As seen in FIG. 24, proximal portion 120' is rotated 180 degrees about the long axis of portion 120' to provide a clear view of an elongated slit 124' which is open at a distal end 126' and closed at a proximal end 128'.

Distally disposed near slit end 126' is a female fitting 140' whereby nose section 122' is connected to portion 120'. In this case, nose section 122' is properly oriented to be joined to portion 120'. (See FIGS. 19–13.) Nose section 122', like nose section 122, has a nose portion 142 which is sized and shaped to provide a stabilizing connection between needle shield 40' and catheter assembly 50. (See FIG. 25.)

Figure 19:
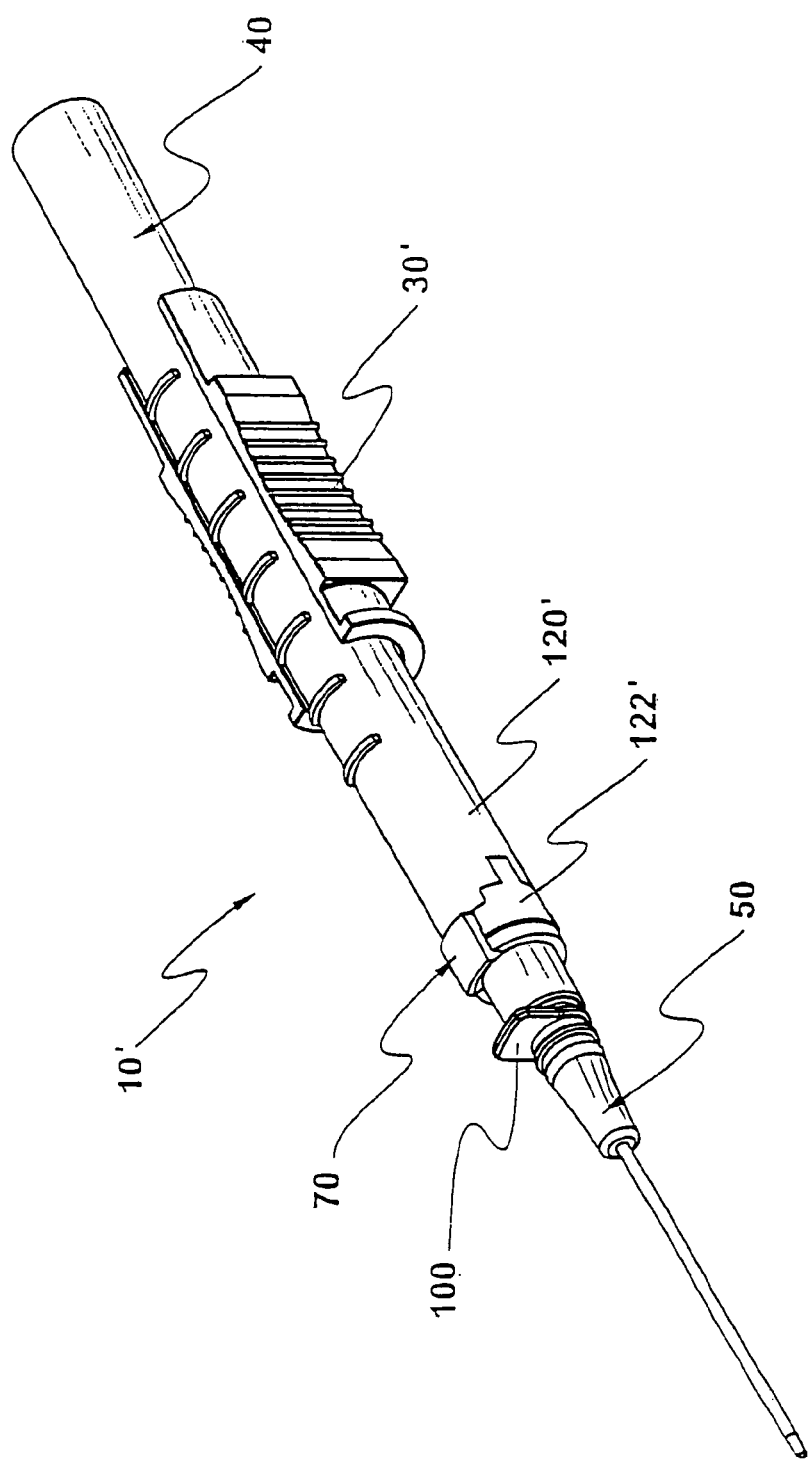
FIG. 19 is a perspective of the device seen in FIG. 18 with a handle displaced to partially withdraw a catheter insertion needle from a distally disposed catheter.
Figure 25:
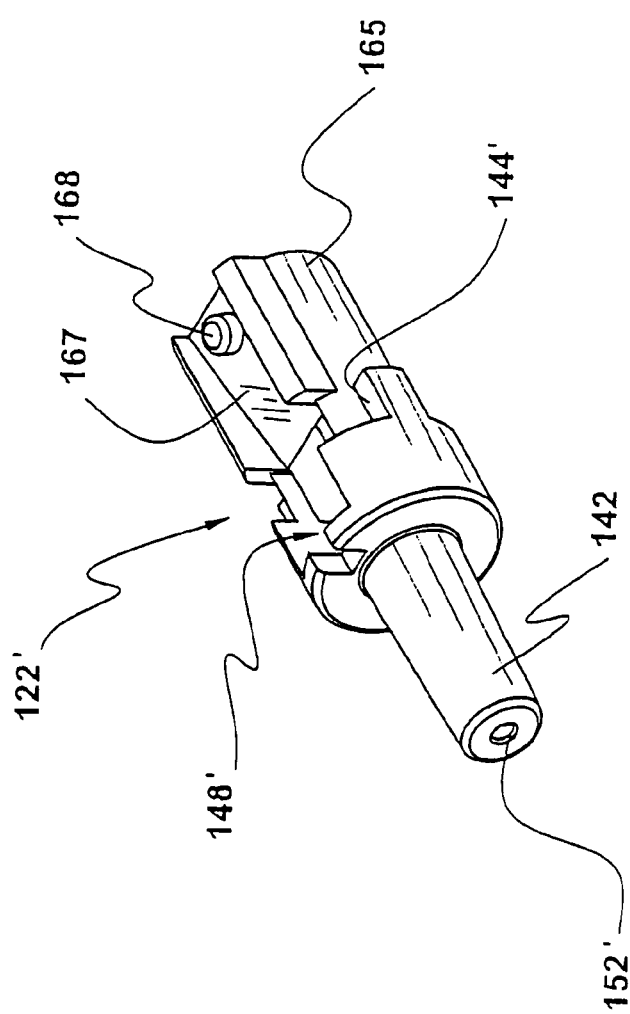
FIG. 25 is a perspective of an interfacing part disposed between the shield and the catheter assembly.

Proximally disposed relative to nose portion 142, in FIG. 25, is a male fitting 144' which is sized and shaped to make a secure joint with fitting 140'. Note that portion 120' has an open flute 146' which coincides with an open flute 148' of nose section 122' to form a slot 150' (see FIG. 20) wherethrough a member 102 (as seen in FIG. 16) of latching part 70 communicates between needle 60 and an edge 96 of catheter assembly 50 (see FIG. 11) to releasibly, but securely join needle shield 40' to catheter assembly 50, as seen in FIGS. 18–20.

Figure 20:
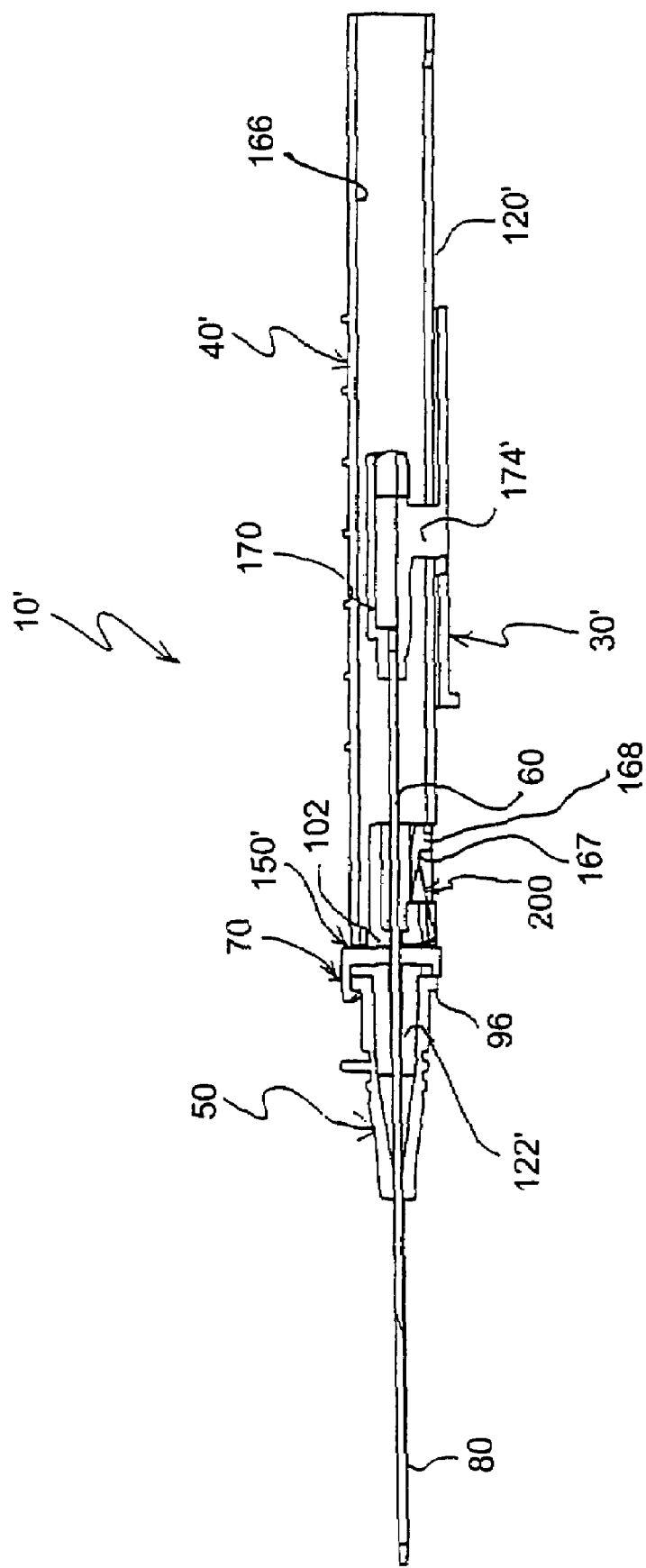
FIG. 20 is a cross section of a side elevation of the device as seen in FIG. 19.

Nose section 122' comprises a proximally disposed surface 165 (see FIG. 25) which corresponds to an interior surface 166 of proximal portion 120' (see FIG. 20). As-best visualized in FIG. 20, nose section 122' has an inferiorly disposed sloped surface 167 which is seen in superior disposition when section 122' is rotated 180 degrees in FIG. 25. A needle tip protective spring clip retention knob 168 is disposed upon sloped surface 167. Knob 168 should have sufficient height and girth to provide for retaining a needle tip protective clip (such as spring clip 200 disclosed hereafter) in tension. Nose section 122' has a through hole 152' which is substantially the same in form and function as through hole 152 in nose section 122.

Handle 30' is like handle 30 (see FIGS. 12–13) in all ways except handle 30' is constructed differently about a stem 174', as seen in FIG. 20. Stem 174' alone provides support for a medially disposed hub 170. As seen in FIG. 20, Handle 30' has no hole in the region of stem 174' for reasons which are disclosed in detail hereafter.

Handle 30' may be made from a wide variety of synthetic resinous materials, but care should be taken to select materials which are clear for a transparent view of hub 170. Further, the selected material should provide either for adhesion or a reliable press fit of needle 60. Similarly, needle shield 40' may be made from a wide variety of synthetic resinous materials, but should also be transparent to provide a clear view of hub 170. Such a material may be polystyrene.

Figure 26:
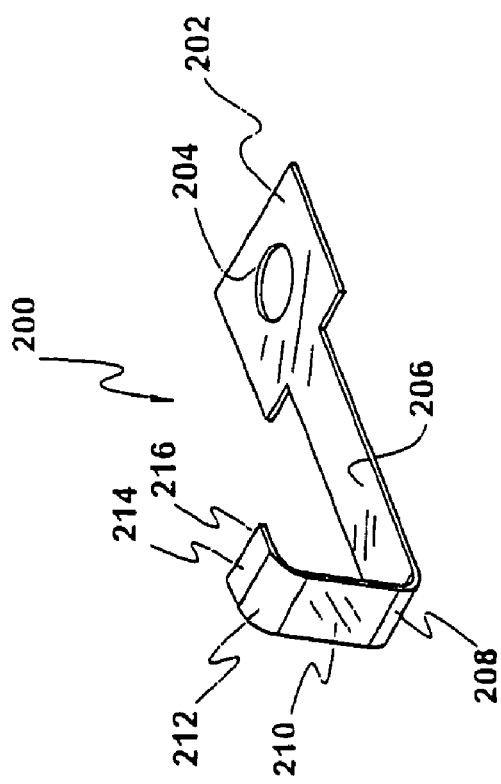
FIG. 26 is a perspective of a clip which is used to mechanically sense the end of the catheter insertion needle and protectively lock the catheter insertion needle inside the needle shield.

Device 10' has a different unreleasible lock than device 10, the variance in unreleasible locks being the primary difference between the two devices. A primary part in the unreleasible lock for device 10' is the (needle tip protective) spring clip 200, seen in FIGS. 20, 22 and 26. Spring clip 200 is seen as an isolated part in FIG. 26. Preferably being made of spring quality stainless steel, on a proximal end, spring clip 200 is formed with a proximally disposed plate 202 having a centered hole 204. Extending distally from plate 202 is a spring arm 206 which ends at a first bend 208 whereat a barrier plate 210 is formed. Superior to plate 210 is a second bend 212 and a shortened proximal extension 214 which ends abruptly at edge 216.

As seen in FIG. 20, spring clip 200 is affixed to knob 168 such that, when insertion needle 60 is disposed through latching part 70, spring arm 206 is held in tension through contact of extension 214 and edge 216 against needle 60. Note, in FIG. 22, when handle 30' is fully retracted relative to needle shield 40', extension 214 and edge 216 no longer contact needle 60 thus freeing arm 206 to relaxively conform to sloped surface 167. This conformance lifts barrier plate 210 in line with needle tip 101 to unreleasibly lock needle 60 inside needle shield 40' for safety. Retraction of needle 60 into safety of needle shield 40' is substantially the same as described above for device 10. Catheter insertion needle 60 is withdrawn from catheter assembly 50 by securing catheter assembly 50 against inadvertent withdrawal, as by holding tab 100. Of course, tab 100 may be used to urge catheter 60 about needle tip 101 as earlier disclosed.

Use of device 10' is identical to use of device 10, although function of some internal processes of device 10' is different than processes of device 10. To make device 10' ready for use, cover 20, seen in FIG. 17, is removed as seen in FIG. 18. Once catheter 80 and insertion needle Go are inserted into a desired predetermined site, generally, catheter assembly 50 is urged distally relative to handle 30, which displaces both catheter assembly 50 and securely affixed needle shield 40'. For this purpose, tab 100 provides a readily accessible appurtenance for forcible and stabilizing access to catheter assembly 50.

Figure 21:
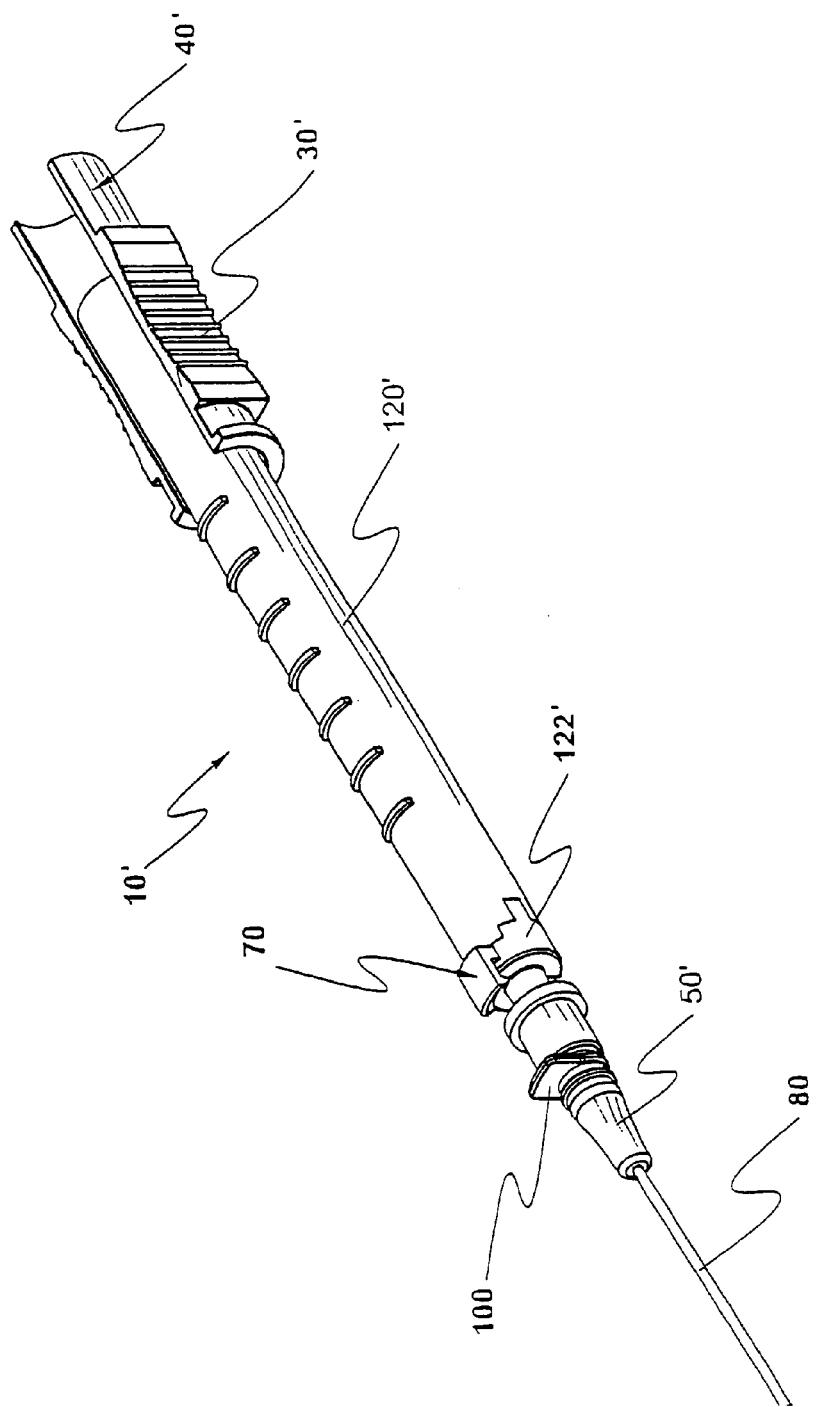
FIG. 21 is a perspective of the device seen in FIG. 19 with the handle further displaced to completely withdraw the catheter insertion needle into safety of a surrounding needle shield.

Once insertion needle 60 is to be withdrawn from catheter 80, stabilizing force is applied to catheter assembly 50, preferably upon the appurtenance, and handle 30' is gripped and displaced proximally as seen in FIG. 19. As seen in the partial retraction of handle 30' in FIGS. 19 and 20, spring clip 200 and latching part 70 are firmly held in place by insertion needle 60. When handle 30' is displaced to its farthest proximal point relative to needle shield 40', as seen in FIGS. 21 and 22, insertion needle 60 is displaced from through hole 110 in latching part 70 which releases needle shield 40' from catheter assembly 50 allowing device 10' to become a passively separated and disposable part, as seen in FIG. 23.

Figure 22:
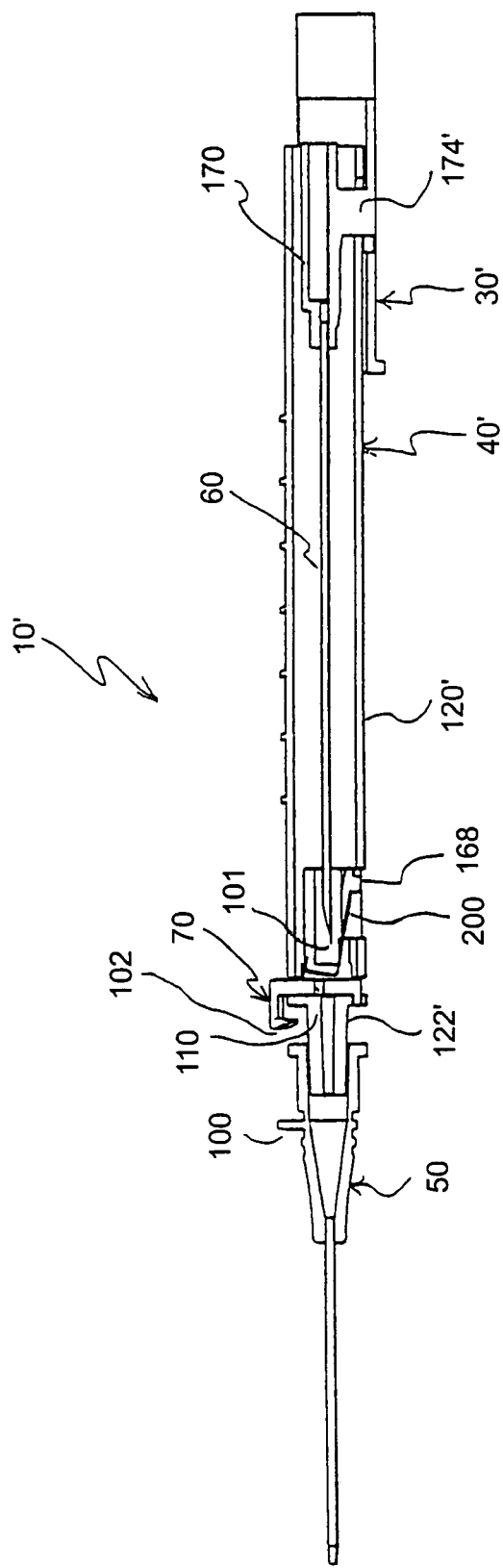
FIG. 22 is a cross section of a side elevation of the device as seen in FIG. 21.
Figure 23:
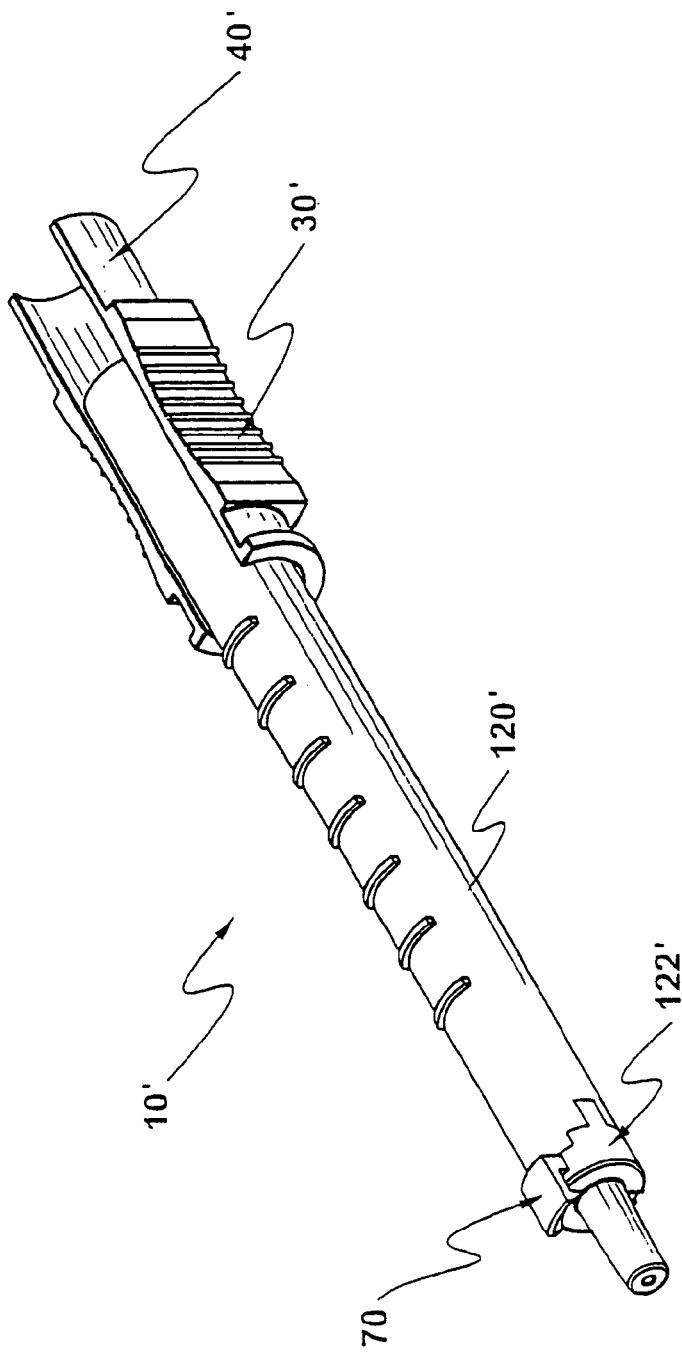
FIG. 23 is a perspective of a separated portion of the device seen in FIG. 21, after being separated and displaced from the catheter assembly.

As may be noted, in FIG. 22, spring clip 200 is released from its stressed state by retraction of insertion needle 60 after clearance of needle tip 101 from through hole 110. As may be noted, it would be preferable to have the release of spring clip 200 either concurrent with or prior to the clearance of needle tip 101 from through hole 110.

Figure 27:
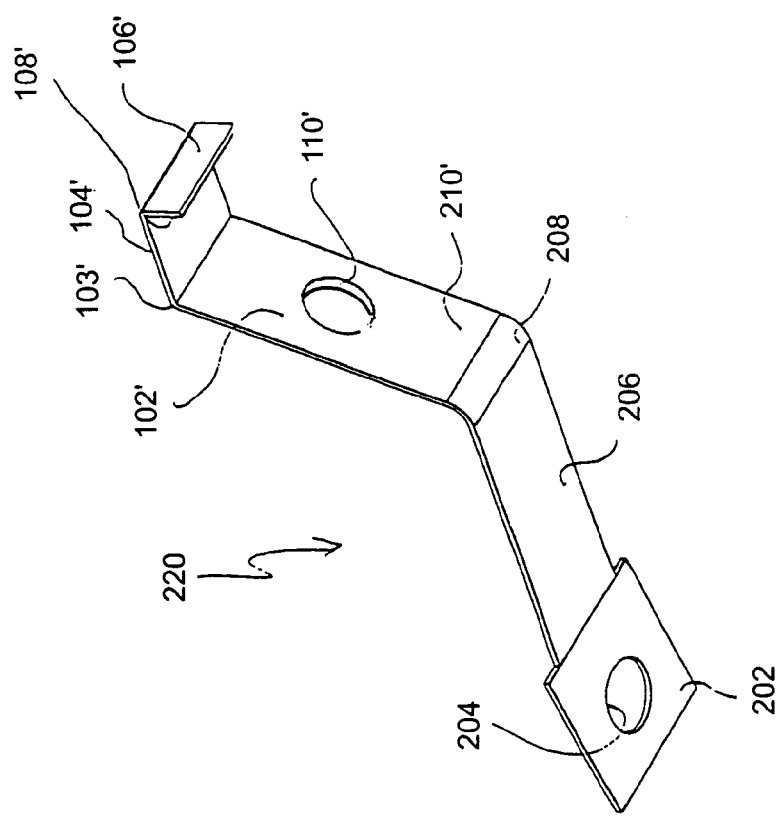
FIG. 27 is a perspective of a part which acts as both a clip and a latch to mechanically sense the end of the catheter insertion needle, lock the catheter insertion needle inside the needle shield and release the needle shield from the catheter assembly.

For this reason, it may be preferable to place barrier plate 210 distal to member 102. While such a placement is not seen in the figures, an equivalent mechanization is accomplished by a single part 220 which combines the functions of spring clip 200 and latching part 70. Part 220 is seen in FIG. 27.

Preferably being made of spring steel and similar to spring clip 200, part 220 is formed with a proximally disposed plate 202 having a centered hole 204. Extending distally from plate 202 is a spring arm 206 which ends at a first bend 208 whereat a barrier plate 210' is formed. However, different from barrier plate 210, barrier plate 210' is inferiorly disposed to a through hole 110'. Barrier plate 210' is contiguous with a superiorly disposed upright member 102' which provides the same function as upright member 102. Similar to upright member 102, upright member 102' terminates superiorly at end 103' with a transversely and distally extending beam 104'. Beam 104' abruptly ends with a downwardly extending flattened tooth 106' which provides a proximally facing latch 108'. Through hole 110' is sized and positioned first to conformably permit catheter insertion needle 60 to slide therethrough and second to hold latch 108' in a secure connection with edge 96 as long as catheter insertion needle 60 remains in through hole 110'. Part 220 is affixed to knob 168 in the same manner spring clip 200 is thereto affixed.

Figure 28:
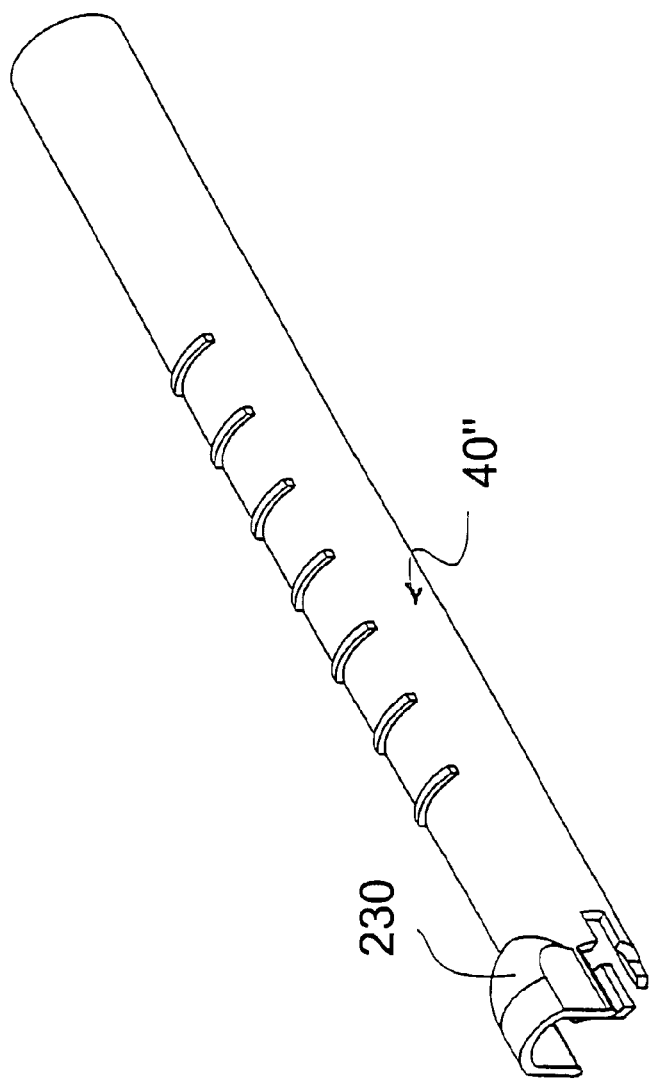
FIG. 28 is a perspective of a needle shield associated with the part seen in FIG. 27.

As part 220 performs the functions of both spring clip 200 and latching part 70 in a device 10" (seen in FIGS. 29 and 30), care should be taken to assure through hole 110' cannot be inadvertently aligned with needle tip 101 after release of spring arm 206 following passage of needle tip 101 through hole 110'. To accomplish this a shroud 230 is added to the structure of needle shield 40' to form a needle shield 40". (See FIG. 28). In all other ways needle shield 40" is substantially the same as needle shield 40'.

Figure 29:
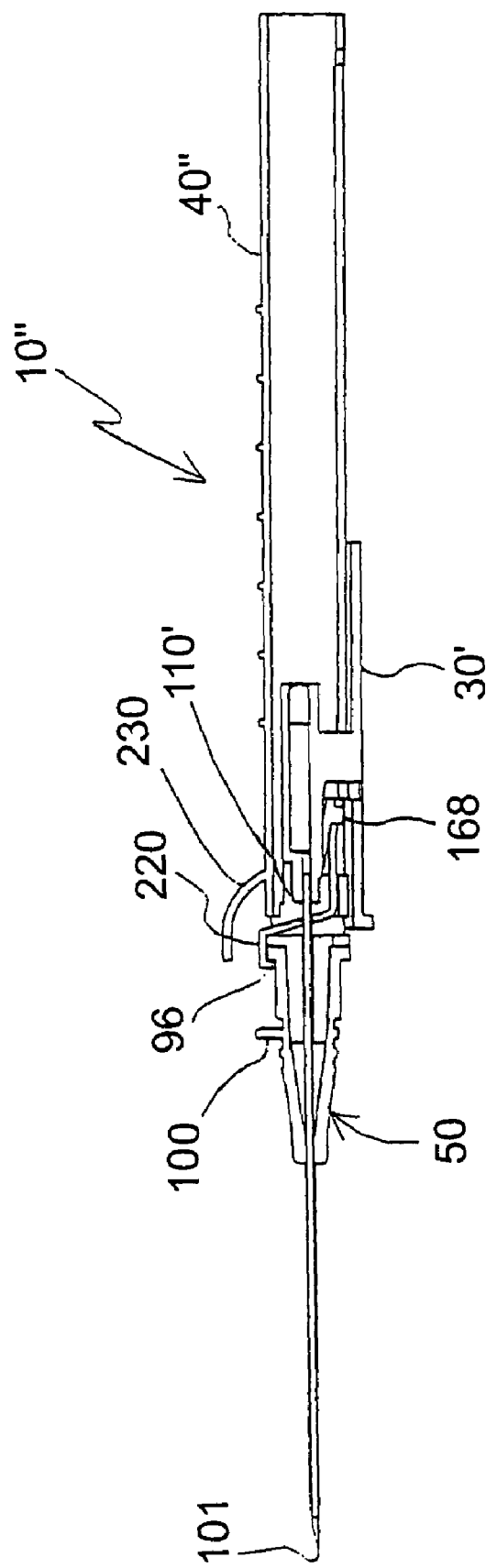
FIG. 29 is a cross section of an embodiment of a device which employs the part seen in FIG. 27 and the needle shield seen in FIG. 28.
Figure 30:
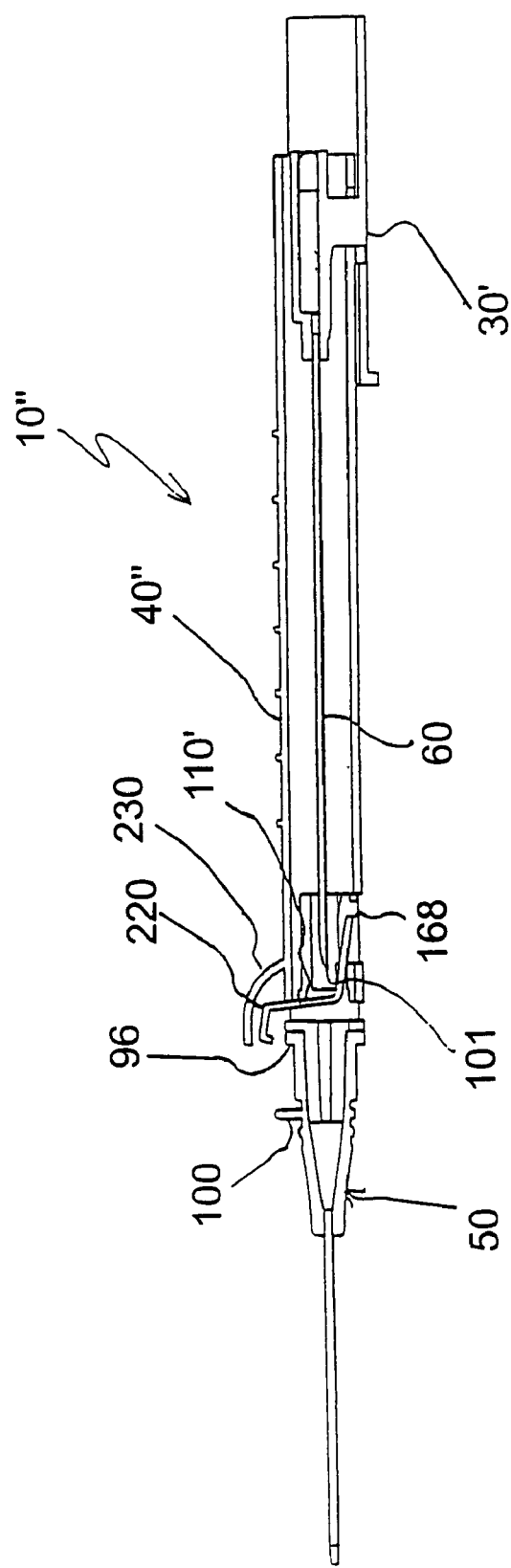
FIG. 30 is a cross section of the device embodiment seen in FIG. 29, but deployed to protect the catheter insertion needle.
Figure 31:
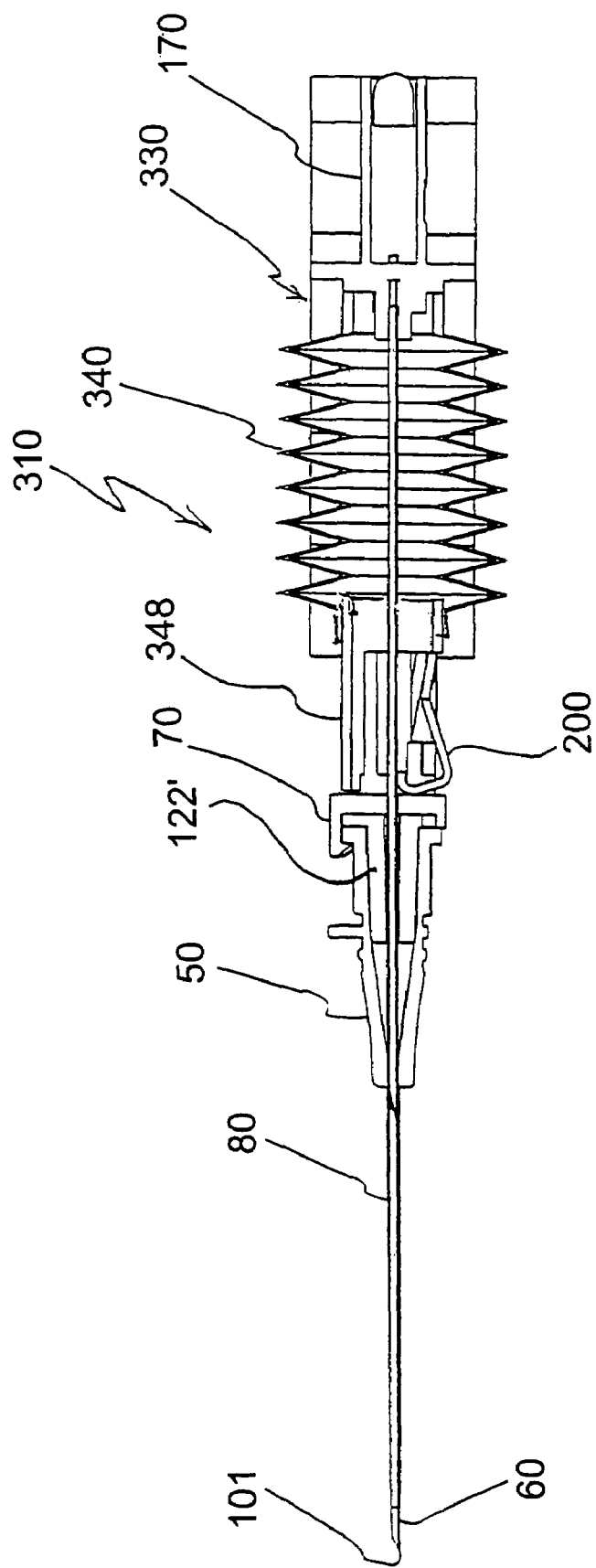
FIG. 31 is a cross section of another embodiment of a device which is shortened through the use of a foldable needle shield.

As may be seen in FIG. 29, part 200 acts to latch catheter assembly 50 securely to needle shield 40" while handle 30' is distally disposed relative to needle shield 40". When handle 30' is displaced to withdraw insertion needle 60 and needle tip 101 from through hole 110', part 200 reactively is displaced superiorly releasing latch 108' from edge 96 permitting passive separation of device 10" from catheter assembly 50.

Another embodiment of the instant invention which provides for a shortened device is seen as device 310 in FIGS. 31-35. In device 310, an elongated, rigid cylindrical structure, such as needle shields 40, 40' and 40" in devices 10, 10' and 10", respectively, is replaced, in-part, by a folding or accordionating shield 340, seen in FIG. 31. A handle 330 has gripping surfaces 160 and 160' for digitary control, but has no need for a track as disclosed for handles 30 and 30'.

Figure 32:
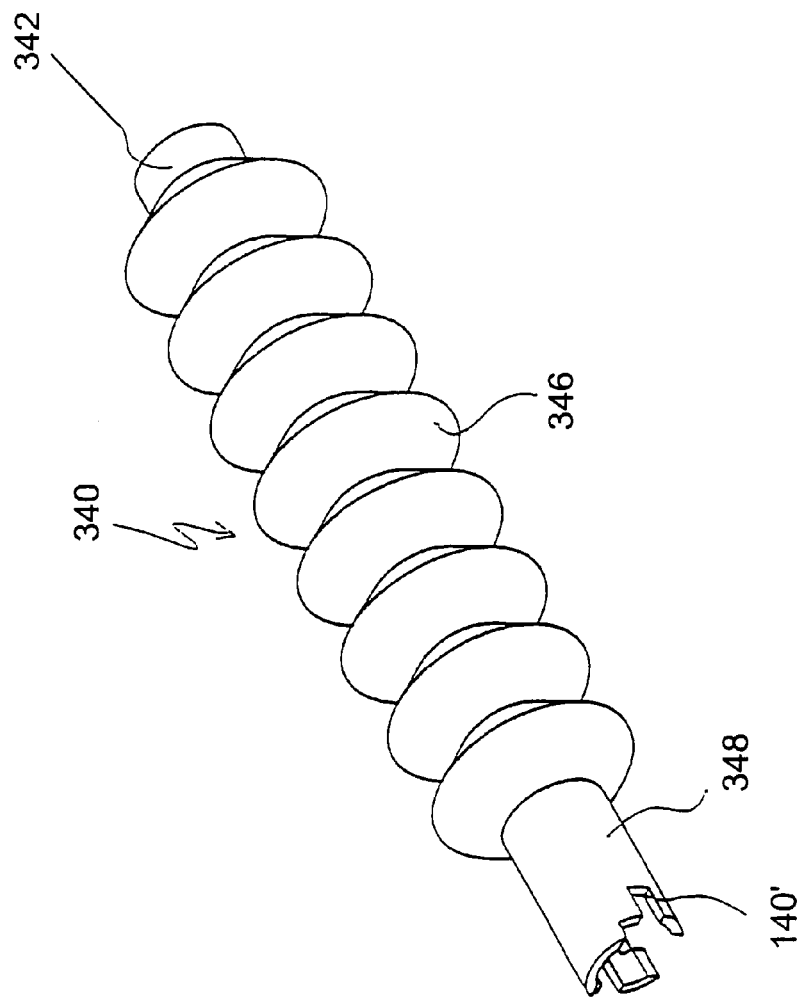
FIG. 32 is a perspective of the needle shield seen in FIG. 31.
Figure 33:
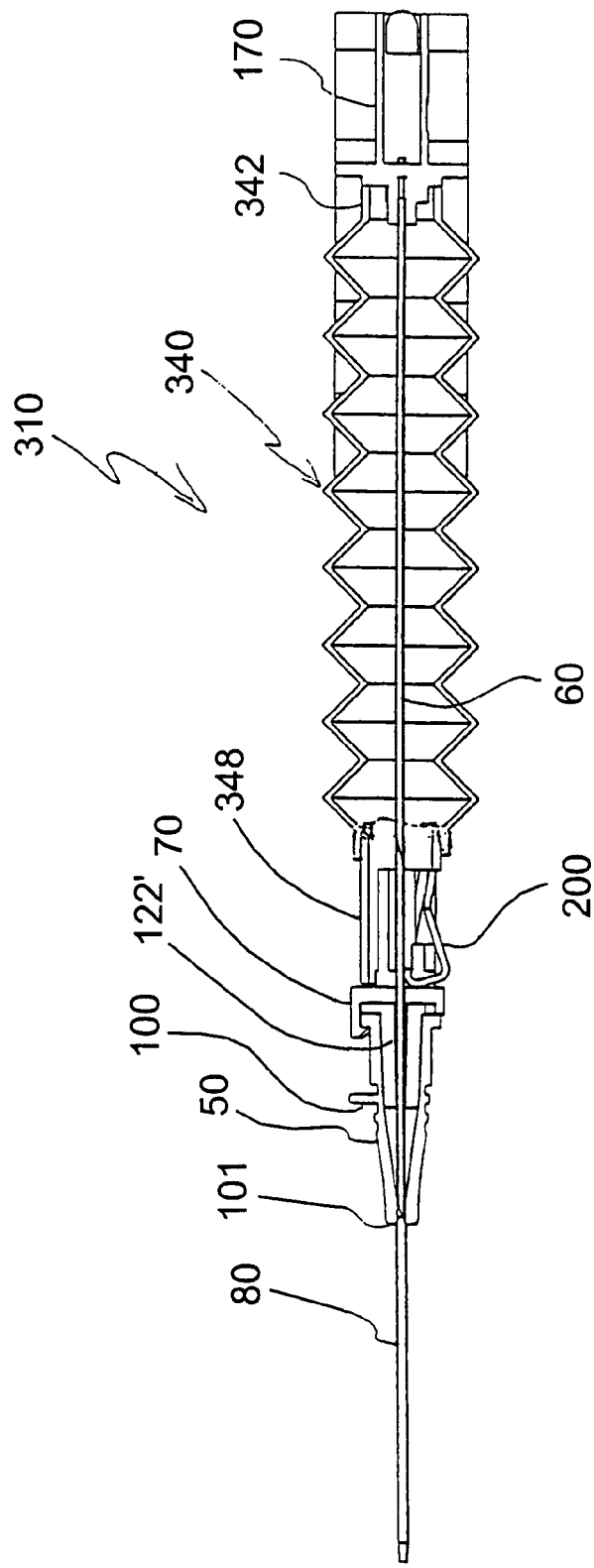
FIG. 33 is a cross section of the device seen in FIG. 31, but having a needle retraction handle displaced to partially withdraw a catheter insertion needle into the needle shield.
Figure 34:
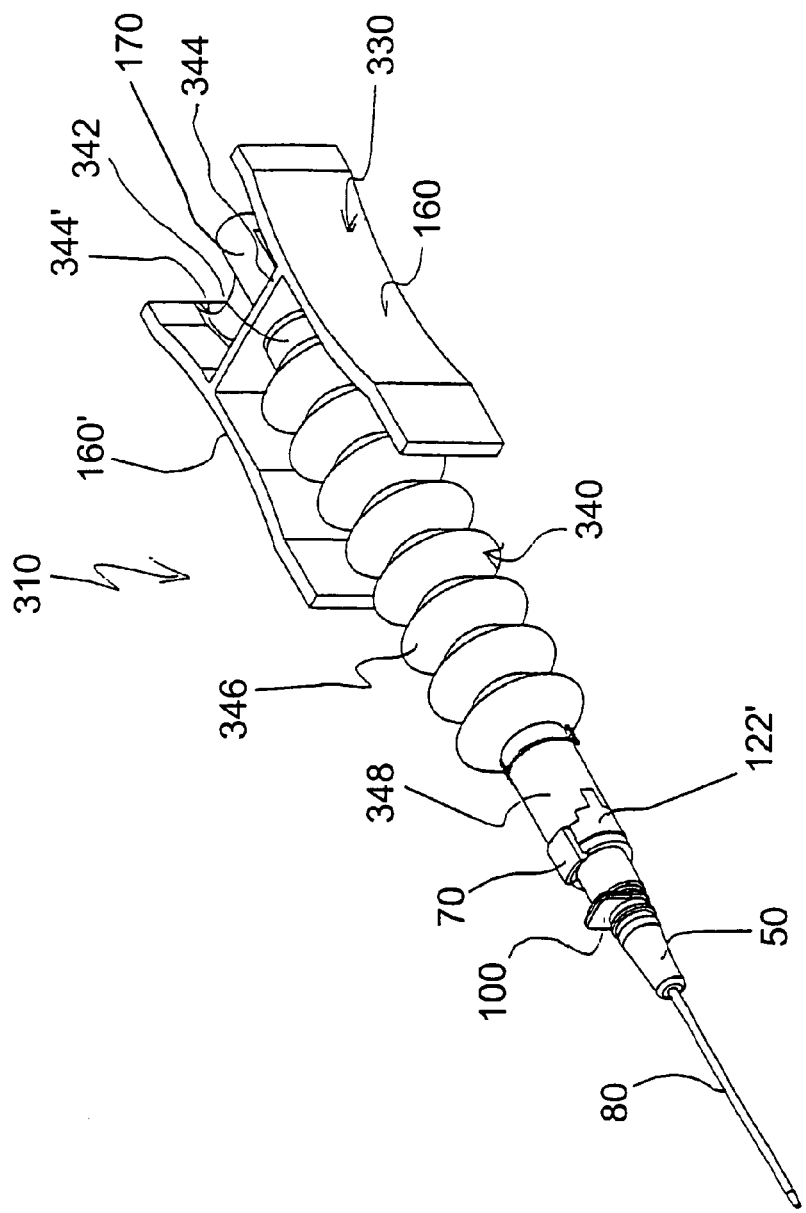
FIG. 34 is a perspective of the device disposed in a manner similar to that of FIG. 33.
Figure 35:
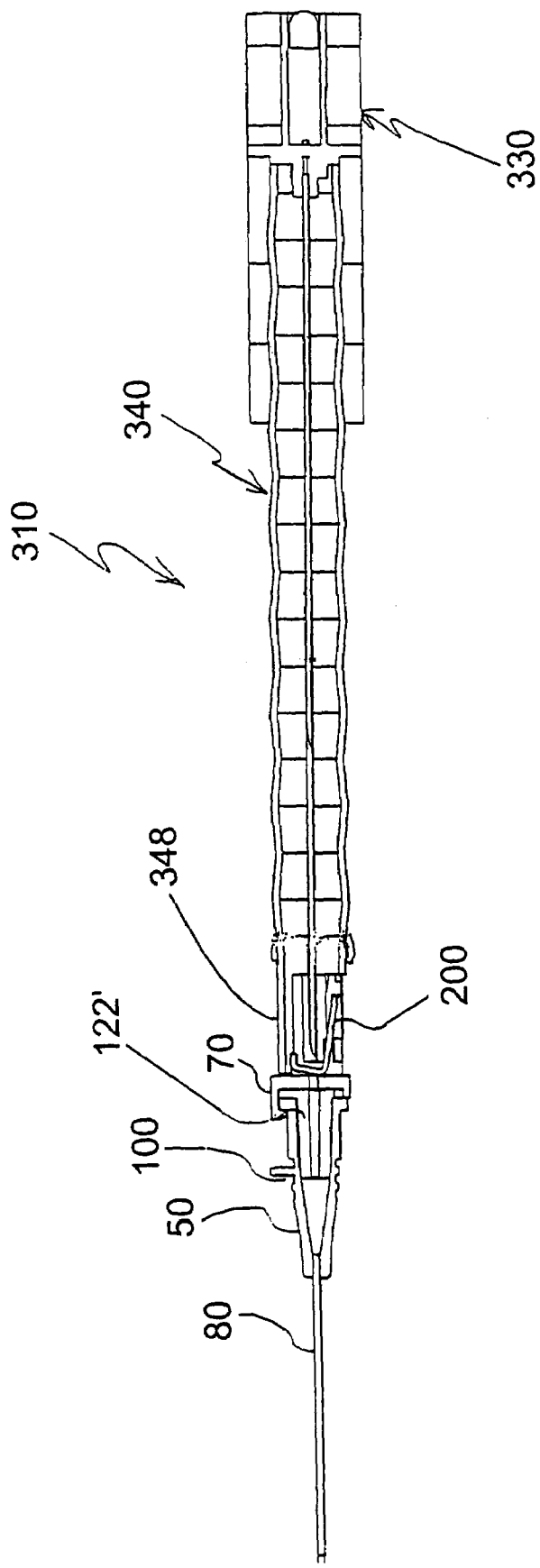
FIG. 35 is a cross section of the device seen in FIG. 31 with the catheter insertion needle fully encased within the needle shield.

As seen in FIG. 32, needle shield 340 most proximally is fitted with a hollow cylindrical hub attachment 342 whereby shield 340 is securely affixed to a hub, such as hub 170 of device 10' seen in FIG. 20. In this embodiment, hub 170 is medially supported between gripping surfaces 160 and 160' by a pair of joined struts 344 and 344', as seen in FIG. 34. Referencing FIG. 32 once more, distally disposed relative to hub attachment 342 is a folded or accordionated segment 346 of needle shield 340. Distal to segment 346 is a needle tip protection, rigid cylindrical segment 348 to which segment 346 is preferably adhesively joined. Segment 348 has a distal connecting face 140" which is identical in form and function with fitting 140' for connecting to nose-section 122'. Note that part 220, seen in FIG. 27, may be used in device 310, to substitute for latching part 70 and clip 200, although such is not shown in the figures.

Hub attachment 342 and segment 346 are preferably made from a sturdy, but foldably compressible polyester (PET) synthetic resinous material, although other foldable materials may be used within the scope of the invention so long as necessary material strength and tethering properties are met which protect insertion needle 60 and tip 101 when retained for protective safety within needle shield 340. All other portions of device 310 may be made from the same materials recommended for device 10, as from which devices 10' and 10" may also be made. The length of segment 346 should be determined by the length required, when extended, to release clip 200 (seen in FIGS. 33 and 35) when needle 60 is retracted, but should be short enough to assure that needle tip 101 is retained within segment 348 when clip 200 is about needle tip 101.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A passively activated safety system used for catheter insertion said system comprising:
    a catheter assembly comprising a catheter and a hub proximally affixed thereto, said hub comprising an attachable fitting, an appurtenance for displacing the catheter relative to the needle and stabilizing the catheter assembly during withdrawal of a catheter insertion needle and a catch whereby the catheter assembly is securely, but releasably, affixed to a needle shield;
    the catheter insertion needle, slidably disposed within the catheter and used to facilitate inserting the catheter into a patient, but removed thereafter, leaving the inserted catheter in place, said needle comprising a distal end having a sharpened tip and a proximal end for connecting to a needle hub;
    a handle for gripping the device, said handle comprising exterior gripping surfaces, an interiorly disposed slide track and the needle hub medially disposed within and aligned with the slide track;
    the needle shield slidably engaged on a proximal end to said handle in line with the insertion needle, said shield comprising a hollow interior and a length adequate to contain said insertion needle;
    said needle shield further comprising a latching part having a latch which firmly joins the shield to the catheter assembly via the catch, a mechanical sensor and actuator which detects full displacement of the catheter insertion needle into protective cover of the needle shield and which passively releases the latch from the catch and therefore the catheter assembly from the catheter insertion needle, the handle and the needle shield when such full displacement occurs;
    a lock disposed with said needle shield which assures the shield is retained in protective engagement about said needle and needle tip upon release of the catheter assembly from the catheter insertion needle, the handle and the needle shield, wherein said lock comprises a spring clip formed with a proximally disposed plate and a spring arm extending distally from said plate, wherein said spring arm is held in tension through contact against said needle when said needle is disposed through said latching part, and said spring arm is freed when said handle is fully retracted relative to said needle shield thereby lifting said plate in line with said needle tip to unreleasibly lock said needle inside said needle shield; and
    a shroud extending from an outside surface of said needle shield to prevent inadvertent engagement with said latch to prevent accidental displacement of said lock.

2. A passively activated safety system according to claim 1 wherein said handle comprises at least one stem by which said needle hub is medically displaced from said track.

3. A passively activated safety system according to claim 2 wherein said at least one stem comprises a proximal stem and a distal stem separated by a predetermined distance.

4. A passively activated safety system according to claim 3 wherein said track comprises a slit disposed lengthwise along said track.

5. A passively activated safety system according to claim 4 wherein said track comprises a pair of arms which meet at a proximally disposed separable juncture.

6. A passively activated safety system according to claim 5 where said lock is formed by said arms at said juncture and the proximal stem.

7. The system according to claim 1 wherein said plate includes a clearance hole substantially centered in said plate wherein said needle is disposed through said hole when said needle is in a distally disposed position and wherein said spring arm biases said hole away from said needle path when said needle is retracted out of said clearance hole thereby blocking subsequent distal displacement of said needle.

8. The system according to claim 7 wherein said spring clip further comprises a latching part engaging said catch when said needle is extended through said through hole and releasing said catch when said needle is withdrawn from said through hole.

9. A passively activated safety system according to claim 1 wherein said needle shield comprises a rigid cylindrical part.

10. A passively activated shielding apparatus for protective safety of a catheter insertion-needle, said apparatus comprising:
    an elongated housing comprising externally accessible sidewalls which are configured for use as handles, the housing further comprising an inwardly disposed surface and a medially disposed catheter insertion-needle hub raised from said surface upon a stem, said surface defining a slide track for guiding an elongated, hollow needle guard therein;
    the catheter insertion-needle affixed on one end to the needle hub and projecting distally to a sharpened tip in alignment with the slide track;
    the elongated, hollow needle guard disposed about at least a portion of the catheter insertion-needle and engaged inside said surface along said track to slide from a first position where the needle guard is displace away from said sharpened needle tip such that the catheter insertion-needle is bared for insertion into a patient to a second position where said needle tip is covered and protected by the needle guard, said needle guard comprising a releasable latching assembly for a catheter hub and a slot wherethrough a latching part is disposed to communicate with the catheter insertion-needle when the catheter insertion-needle is unprotected by the needle guard;

a catheter assembly comprising an elongated catheter, sized to be disposed about said catheter insertion-needle for insertion, and a luer type hub whereby said catheter is aligned with and securely, but releasably, affixed to said latching assembly, said hub comprising a raised proximal portion, having an edge which acts as a catch, and a tab for displacing the catheter assembly relative to the elongated housing;

the latching part, disposed to fit through the slot to thereby provide an external segment, which communicates with the proximal edge portion of the luer type hub to form the latching assembly, and an internal segment which is disposed to communicate with the catheter insertion-needle, the external segment comprising a latch for said catch and the internal segment comprising a hole through which the catheter insertion-needle passes and by which the catheter insertion-needle maintains sufficient stress upon the latching part to cause the latch and catch to remain securely affixed until the catheter insertion-needle is displaced sufficiently far within the needle guard for safety to the second position whereat the catheter insertion-needle and sharpened needle tip clear the hole relieving the stress on the latching part which responsively releases the latch from the catch permitting the housing, guard, catheter insertion-needle and latching part to be passively displaced away from the catheter assembly by the act of simply pulling the catheter insertion-needle out of the catheter assembly;

a lock disposed with said needle guard which unreleasibly secures the catheter insertion-needle inside the needle guard for safety, wherein said lock comprises a spring clip formed with a proximally disposed plate and a spring arm extending distally from said plate, wherein said spring arm is held in tension through contact against said needle when said needle is disposed through said latching part, and said spring arm is freed when said housing is fully retracted relative to said needle guard thereby lifting said plate in line with said needle tip to unreleasibly lock said needle inside said needle guard; and a shroud extending from an outside surface of said needle guard to prevent inadvertent engagement with said latch to prevent accidental displacement of said lock.

11. The apparatus according to claim 10 wherein said plate includes a clearance hole substantially centered in said plate wherein said needle is disposed through said hole when said needle is in a distally disposed position and wherein said spring arm biases said hole away from said needle path when said needle is retracted out of said clearance hole thereby blocking subsequent distal displacement of said needle.

12. The apparatus according to claim 11 wherein said spring clip further comprises a latching part engaging said catch when said needle is extended through said through hole and releasing said catch when said needle is withdrawn from said through hole.

13. The apparatus according to claim 12 wherein said needle guard further comprises a shroud protruding from an outside service of said needle shield said shroud covering external parts of said spring clip to prevent accidental displacement of said spring clip and inadvertent alignment of said through hole with said needle tip after said spring arm is released.

14. A method for passively activating a safety shield while withdrawing a catheter insertion-needle from a hypodermically inserted catheter comprising the steps of:

providing:

an elongated housing comprising externally accessible finger grips, the housing further comprising a medially disposed catheter insertion-needle hub and a slide track for guiding an elongated, hollow needle guard therein;

the catheter insertion-needle affixed on one end to the needle hub and projecting distally to a sharpened tip in alignment with the slide track;

the elongated, hollow needle guard engaged to slide linearly along said track from a first position to a second position, said needle guard comprising a releasable fitting for a catheter hub and a slot wherethrough a latching part is disposed for communicating with the catheter insertion-needle;

a catheter assembly comprising an elongated catheter, sized to be disposed about said catheter insertion-needle for insertion, and a luer type hub whereby said catheter is aligned with and securely, but releasibly, affixed to said fitting, said luer type hub comprising a raised edge which acts as a catch, and a digitally accessible member;

the latching part, disposed to fit through the slot to thereby provide an external segment, which communicates with the raised edge, and an internal segment which is disposed to communicate with the catheter insertion-needle, the external segment comprising a latch for said catch and the internal segment comprising a hole through which the catheter insertion-needle passes and by which the catheter insertion-needle maintains sufficient stress upon the latching part to cause the latch and catch to remain securely affixed;

a lock disposed with said needle guard which unreleasibly secures the catheter insertion-needle inside the needle guard for safety, wherein said lock comprises a spring clip formed with a proximally disposed plate and a spring arm extending distally from said plate, wherein said spring arm is held in tension through contact against said needle when said needle is disposed through said latching part, and said spring arm is freed when said handle is fully retracted relative to said needle shield thereby lifting said plate in line with said needle tip to unreleasibly lock said needle inside said needle shield; and a shroud extending from an outside surface of said needle guard to prevent inadvertent engagement with said latch to prevent accidental displacement of said lock;

inserting said catheter insertion-needle and catheter into a patient;

assuring the catheter is properly positioned at a predetermined site;

while applying restraining force to assure the catheter stays at the predetermined site, applying proximally directed force at the finger grips thereby displacing the catheter insertion-needle, proximally relative to the stationary catheter, into the needle guard until the catheter insertion-needle is disposed, sufficiently far within the needle guard to protect the needle tip, at the second position and to clear the hole relieving the stress on the latching part which responsively releases the latch from the catch permitting the luer type hub to be separated from the fitting allowing the housing, guard, catheter insertion-needle and latching part to be passively displaced away from the catheter assembly by the act of simply pulling the catheter insertion-needle out of the catheter assembly; and concurrently, within the applying step, unreleasibly locking the needle guard relative to the housing to assure needle safety.

* * * * *